US011138861B2

(12) United States Patent
Blatt et al.

(10) Patent No.: US 11,138,861 B2
(45) Date of Patent: Oct. 5, 2021

(54) EASILY CUSTOMIZABLE INHABITANT BEHAVIORAL ROUTINES IN A LOCATION MONITORING AND ACTION SYSTEM

(71) Applicants: Robert Blatt, Cherry Hill, NJ (US); Frederick Bresani, Southampton, NJ (US)

(72) Inventors: Robert Blatt, Cherry Hill, NJ (US); Frederick Bresani, Southampton, NJ (US)

( * ) Notice: Subject to any disclaimer, the term of this patent is extended or adjusted under 35 U.S.C. 154(b) by 0 days.

(21) Appl. No.: 15/989,330

(22) Filed: May 25, 2018

(65) Prior Publication Data
US 2018/0365965 A1 Dec. 20, 2018

Related U.S. Application Data

(60) Provisional application No. 62/511,182, filed on May 25, 2017.

(51) Int. Cl.
*G08B 21/22* (2006.01)
*A61B 5/00* (2006.01)
*G08B 21/04* (2006.01)
*G08B 25/01* (2006.01)
(Continued)

(52) U.S. Cl.
CPC ............. *G08B 21/22* (2013.01); *A61B 5/00* (2013.01); *A61B 5/1123* (2013.01); *G08B 21/0423* (2013.01); *G08B 25/016* (2013.01); *A61B 5/022* (2013.01); *A61B 5/1118* (2013.01); *A61B 2505/07* (2013.01); *A61B 2560/0242* (2013.01)

(58) Field of Classification Search
CPC ...... G08B 21/22; G08B 21/0423; A61B 5/00; A61B 5/1123; A61B 5/022; A61B 5/1118; A61B 2505/07; A61B 2560/0242
See application file for complete search history.

(56) References Cited

U.S. PATENT DOCUMENTS 9,305,450 B2 * 4/2016 Halverson .............. G08B 25/00
9,734,295 B1 * 8/2017 Movva .................... G16H 70/60
(Continued)

FOREIGN PATENT DOCUMENTS

EP 3163545 A1 5/2017

*Primary Examiner* — Quan-Zhen Wang
*Assistant Examiner* — Mancil Littlejohn, Jr.
(74) *Attorney, Agent, or Firm* — Wolf, Greenfield & Sacks, P.C.

(57) ABSTRACT

A virtual care system. The system identifies movement and status (e.g., location, time duration in a location, direction of movement, last activity) of an inhabitant of a premises, and takes actions based on the identified movement and status. The system includes an activity plan comprising a plurality of activity primitives. Each activity primitive comprises a time window, and classifies movements and/or activities of the inhabitant as, for example, expected or unexpected or abnormal patterns of behavior, based on occurrence and/or absence of output from a single sensor or paired sensors at the premises in the time window. The system is configured to notify caregivers with different levels of urgency (e.g., informational or warning to critical) based on the classifications of the detected movements and/or activities, and/or to take other actions such as turning off the lights and locking the door.

23 Claims, 23 Drawing Sheets

(51) Int. Cl.
*A61B 5/11* (2006.01)
*A61B 5/022* (2006.01)

(56) References Cited

U.S. PATENT DOCUMENTS

| | | | | |
|---|---|---|---|---|
| 2004/0030531 | A1* | 2/2004 | Miller | A61B 5/0002 |
| | | | | 702/182 |
| 2008/0256445 | A1* | 10/2008 | Olch | G16H 40/67 |
| | | | | 715/700 |
| 2009/0237245 | A1* | 9/2009 | Brinton | G07C 5/008 |
| | | | | 340/540 |
| 2010/0053867 | A1* | 3/2010 | Ellis | A61B 5/0205 |
| | | | | 361/679.03 |
| 2010/0331627 | A1* | 12/2010 | Thukral | G16H 20/10 |
| | | | | 600/300 |
| 2013/0217352 | A1* | 8/2013 | Pan | A61B 5/1112 |
| | | | | 455/404.1 |
| 2015/0164376 | A1* | 6/2015 | Huang | G06F 19/3468 |
| | | | | 600/302 |

* cited by examiner

| ActNum 1201 | ActivityType 1202 | DeviceScope 1203 | TimeWin Type 1204 | Event Time 1205 | TimeWin Size (minutes) 1206 | Offset Capable 1207 | Enabled TimeWindow 1208 | Activity Example | Action type (default) 1209 |
|---|---|---|---|---|---|---|---|---|---|
| 1 | premiseActivityNow 1216 | device | uxNoEtw | 3:30PM | 60 | Yes | 3PM - 4PM 1210 | Notify immediately on device activation | : |
| 2 1219 | sequencedActivity | paired 1217 | uxEtw | anytime | 45 | No | Event time of first device + TimeWinSize 1211 | first device event sets timer for setting a second confirming event that must occur before timer ends and TimeWindow occurs | WTC 1212 |
| 3 | premiseActivity | device or premise 1213 | exEtw | 10PM | 120 | Yes | 9PM - 11PM | Bedtime check-in | WTC |
| 4 | premiseActivity | device or premise | exEtw | 8AM | 120 | Yes | 7AM - 9AM | Morning check-in | WTC |
| 5 1218 | premiseActivityNow | device or premise | uxNoEtw | anytime | N/A | N/A | None | Frontdoor (unexpected visitor at wrong time) | WTC |
| 6 1220 | tempMotion | paired | uxEtw | anytime | 45 | No | Time of temp sensor event + TimeWinSize | temp sensor activation paired to motion sensor | WTC |
| 7 1221 | contactMotion | device 1214 | uxEtw | anytime | 10 | No | Time of contact sensor event + TimeWinSize | Exit door opened and checking for premise activity | : 1215 |
| 8 1222 | motionMotion | paired | uxEtw (synthetic) | anytime | 30 | No | Time of motion sensor event + TimeWinSize | Up or down stairs | WTC |
| 9 1223 | premiseActivity | device or premise | exEtw (synthetic) | anytime | 30 (grace period) 1225 | Yes | 12:00AM - 11:59PM | (Nap period) tolerable 'no activity' grace period for given TimeWindow | WTC |
| 10 | premiseNoActivity | device or premise | uxEtw (synthetic) | anytime | 30 (grace period) | Yes | 12:00AM - 11:59PM | tolerable 'no activity' grace period for entire day | A |

FIG. 12A

EASILY CUSTOMIZABLE INHABITANT BEHAVIORAL ROUTINES IN A LOCATION MONITORING AND ACTION SYSTEM

CROSS REFERENCE TO RELATED APPLICATIONS

This patent application claims priority to and the benefit of U.S. Provisional Patent Application Ser. No. 62/511,182, filed on May 25, 2017 and entitled "Easily Customizable Inhabitant Behavioral Routines in a Location Monitoring and Action System," which is hereby incorporated herein by reference in its entirety.

TECHNICAL FIELD

This patent application relates generally to methods and apparatus for identifying an inhabitant's activity on a premises and taking actions corresponding to the identified activity. The inhabitant may be one or more humans and/or pets.

BACKGROUND

One of the challenges of an aging population is to provide adequate care throughout the stages of declining health. The burden of care is increasingly becoming a growing problem as the number of seniors is rising faster than the younger caregiving population. According to the Pew Research Center, just over 1 of every 8 Americans aged 40 to 60 is both raising a child and caring for a parent. In addition, between 7 to 10 million adults are caring for their aging parents from a long distance.[1] US Census Bureau statistics indicate that the number of older Americans aged 65 or older will double by the year 2030, to over 70 million.[2] Many people living alone are either too healthy to transition to an assisted care facility or lack the financial resources. Research also shows that given the option, seniors prefer to age in place.

[1]"Growing Number of People Living Solo Can Pose Challenges", Sep. 11, 2014 by Tim Henderson
[2]United States Census Bureau: https://en.wikipedia.org/wiki/United—States—Census—Bureau Furthermore, personal emergency response systems (PERS) are simply failing to provide an acceptable level of efficacy. According to one National Institute of Health Study, 97% of PERS subscribers never activated a response service after falling and were down for at least an hour.[3]

[3]"Older Homebound Women: Sharing the Risk with Age-Peers of Being Unable to Reach Help Quickly", December 2012, http://www.ncbi.nlm.nih.gov/pmc/articles/PMC3521502/pdf/nihms422136.pdf

BRIEF SUMMARY

Aspects of the present disclosure relate to a Virtual Care System that identifies an inhabitant's movement and status on a home or premises as, for example, expected, unexpected but normal, or unexpected abnormal activity, and notifies caregivers/care partners/notification observers about the movement and status of care receivers/inhabitants within the home or premises.

Some embodiments relate to a monitoring system configured to identify movement and status (location, time duration in a location, direction of movement, last activity) of an inhabitant of a premises. The system may comprise a data store comprising an activity plan comprising a plurality of primitives that define a model activity pattern for the inhabitant, and at least one computing device coupled to the data store. The at least one computing device may be configured to send to at least one controller at the premises a portion of the activity plan; and to receive from at least one controller at the premises notifications based on sensor data captured at the premises indicating human physical motion consistent with or in conflict with the activity plan.

In some embodiments, a method of operating an alerting/notification system programmed with at least one activity primitive characterizing a potential activity of an occupant of a premises. The method may comprise receiving data from a plurality of sensors, processing the received data to identify occurrence of an event associated by the at least one activity primitive, and selectively sending at least one message to one or more notification observers of the alerting/notification system, in accordance with the at least one activity primitive and the received sensor data.

In some embodiments, at least one non-transitory computer-readable medium comprising computer executable instructions that, when executed by at least one processor in a controller coupled to a plurality of sensors at a premises, may perform a method of monitoring activity of a human within the premises. The method may comprise receiving over a network a plurality of activity primitives. Each activity primitive may comprise a time window, and an indication of an activity detectable based on outputs of the plurality of sensors. The method may further comprise, based on the outputs of the plurality of sensors and the plurality of action primitives, communicating over the network notifications of occurrence of non-occurrence of activities associated with the plurality of activity primitives.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 12A is a schematic diagram illustrating a Sample Activity Plan, showing the Implementation of the Activity Primitives with supporting Time and Notification Parameters, according to some embodiments.

DETAILED DESCRIPTION

Figure 1:
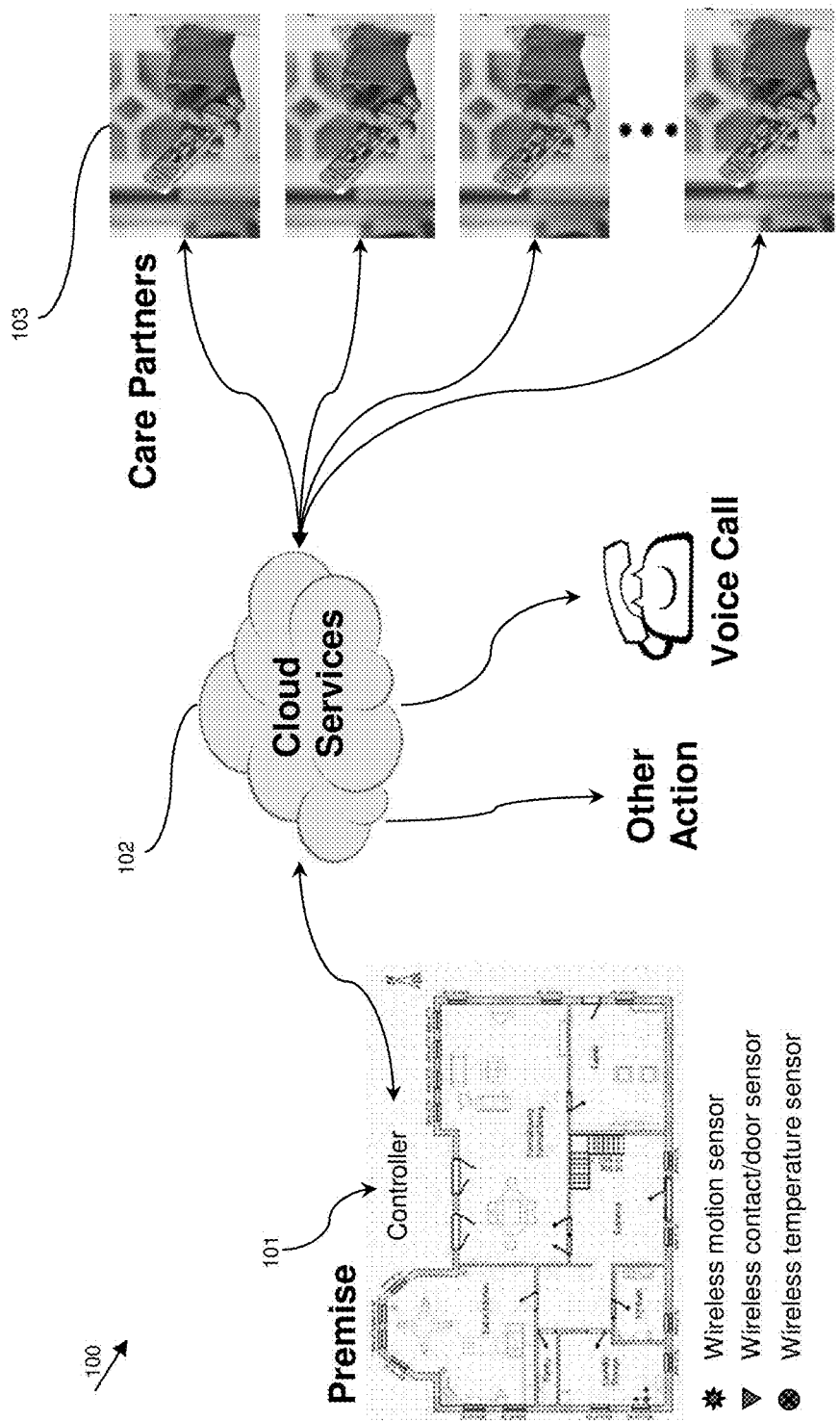
FIG. 1 is a schematic diagram illustrating a virtual care system, according to some embodiments.

The inventors have recognized and appreciated the challenges to provide adequate care to an aging population since the number of seniors is rising faster than the younger caregiving population. Currently, caregivers and care partners, typically family members and close friends (but can also be paid health aides), will remain in close contact with the care receivers, effectively monitoring their activities as a proxy for wellbeing. Without frequent monitoring, making sure that normal daily living activities remain ongoing and consistent cannot be assured nor can data be collected over time and analyzed for positive or negative trends in the care receiver's wellbeing.

The inventors have recognized and appreciated that a Virtual Care System may alleviate the problems for caring the aging population. A Virtual Care System may identify an inhabitant's movement and status on a home or premises as, for example, expected, unexpected but normal, or unexpected abnormal activity, and notify caregivers/care partners/notification observers about the movement and status of care receivers/inhabitants within the home or premises.

The home (or premises) may be any location with sensors (e.g., motion, open/close, temperature, moisture sensors), installed or wearable, that are monitored through on premises coordinating controller. A combination of sensor pairing, time windows (or specific time periods), and a method of detection and notification, which may also be referred to as intelligent monitoring, may be implemented to alert caregivers, care partners and notification observers about the current state of expected and unexpected movements associated with the care receiver or inhabitant being observed by the sensors. The Virtual Care system may also interpret these movements to determine the activity or general wellbeing of the care receiver (inhabitant). In some embodiments, these movements may be interpreted by the caregiver or notification observers.

For example, in a typical living alone scenario, care partners, through daily discussions and interactions with care receivers are typically very knowledgeable of the care receivers habits in terms of when and where specific activities occur. Typical of most people, as people age, their activity patterns become more consistent, thus improving the caregiver/care partner's ability to more accurately anticipate an expected behavioral pattern. Caregivers who are familiar with the patterns can develop an activity profile (Activity Plan) that describes their living pattern as a set of separate independent movements. These movements can be intelligently monitored and exceptions can be detected which in turn can alert a care team of this exception.

Movement and activity may be interchangeable definitions as they describe behavioral patterns that care partners and notification observers are free to interpret or associate when movement is detected within a known context (e.g., moving to a bedroom at an expected bedtime can be interpreted as the activity of going to bed). In addition to movement patterns, information regarding inhabitant status defined as inhabitant location and time duration in said location may be made available to the caregivers and any notification observers.

The system may combine physical sensor events and synthetic sensor events (e.g., events considered time relevant but not generated by physical sensors) with static and dynamically created event time windows to monitor behaviors or routines. The system may define warning periods that are analyzed and monitored to create a progressively escalating notification system. The system may also provide an approach for triggering actions.

Human activities (or movements) may be described and implemented as activity primitives (or methods), each individually configured to describe desired activity milestones (e.g., going to bed, getting up, going safely in and out of bathrooms, leaving/entering the premise, attended cooking, eating). When an activity or an exception is detected from the desired activity, a series of alerts (and/or actions) may be optionally generated (based on the activity configuration) allowing an observing care partner to provide acknowledgement to reset the alert to default, returning the desired activity to its initial normal state (exception removed).

Along with recognizing when activity is detected within the premises, the activity primitives may include constructs for creating time windows and 'no activity' grace periods where alerts are generated when 'no activity' is an activity notifiable abnormal status. The activity primitives may also support the definition of time windows where 'no activity' is an acceptable activity and alerts are not generated.

Through the adaptive combinations of activity primitives, device pairing, event time windows and action type, an administrator can define a customized activity plan that is unique to the care receiver. From the activity plan and the notification delivery system, the Virtual Care System may act as a virtual peer member of the care team.

In some embodiments, a system may capture and disseminate information regarding observed human activity using a combination of events actuated by connected sensors that bi-directionally communicates and relays status to a controller configured in a defined living area or premise. Such a system pertains to a variety of use cases. However, illustrated here is a use case for the industry of care giving/care partnering where those providing the care can define a particular set of expected human activities of the care receiver (person being observed by the sensors) through defined sensor sequences. These activities can be observed through activation of the sensors which results in prescribed levels of notifications to the caregivers. The notifications can be the results of expected activity milestones or the failure of meeting same milestones. The care partner or caregiver can classify the notifications to be either informational (INFO), or warning to critical (WTC) in nature with a progression of urgency from warning to critical if the receivers (caregivers/care partners) of the notifications fail to respond to the system notifications. Notification classifications, in addition to actions, are defined as part of a set of parameters within activity profiles, also referred to as activity plans. Activity plans may be developed by caregivers/care partners using a set of activity primitives requiring additional parameters of sensor names and event time windows in addition to one of the action types (action, informational, warning, critical).

In some embodiments, a system may allow a user to describe activities, monitoring movement, and a framework for notifying caregivers and triggering actions that are, for example, in a format that may be readily accessed and applied by a computer. When fully described in terms of sensors, time windows and action types, a specific activity may become a single entry of an activity plan. In describing the activities, action types play an important role in describing individual activities. Activities that occur within one time window may have a different contextual meaning in another time window.

The activity primitive may comprise a time window and classify movement and/or activity of the inhabitant as either an expected or abnormal patterns of behavior based on occurrence and/or absence of outputs from the plurality of sensors in the time window.

Activity primitives may include a time window and classify movement and/or activity of the inhabitant as either expected or abnormal patterns of behavior based on occurrence and/or absence of outputs from the plurality of sensors in the time window. The sensor output may include receiving data from a combination of sensors specified in conjunction with the activity primitive definitions.

An example would be two activities that monitor the activity of 'leaving the premises'. Leading the premise at 1 PM in the afternoon may be an expected activity for that time of day. That same activity occurring at 1 AM may be an undesirable or abnormal activity. In this context, an activity that supports an action type for 1 PM may be simply informative while the 1 AM activity definition would reflect, the majority of time, an action type of either warning or critical.

Using combinations of a finite number of activity primitives, for example, seven activity primitives (or methods) in the exemplary embodiment described herein, with a single sensor, combinations of sensors, multiple time windows, and action type of either informative or warning to critical, a fully described activity plan can be adapted by adding or removing specific activities represented as single entries that in total represent the care receiver's activity plan.

In some embodiments, a system may include an application that uses a combination of events actuated by connected sensors that bi-directionally communicates and relays status to a controller configured in a defined living area or premises and connected through standard internet protocols to a central web server. The controllers may be programmed by the webserver's activity engine to return activity notifications to the web server when sensor events, associated with specific activities, are activated by human activity or activity that is expected but did not occur. The web server may receive controller events and deliver the notification data to the registered users (caregivers/care partners) of the application.

In some embodiments, the system may include an activity plan editor, which provides a flexible, adaptive way to update, insert, and modify the existing activity plan in the controller. The activity editor first modifies a copy of the controller's activity plan in the application executing on a server remote from some or all of the controllers in the system. The updated activity plan is uploaded to the specific controller where it is reinitialized by the controller. The administrator of the plan may be a caregiver who is assigned primary caregiver status for accessing the application executing on the server. Modifying and changing the plan may require primary caregiver designation.

In some embodiments, the system may receive user input specifying an activity plan in the form of a finite number of activity primitives, for example, seven (7) activity primitives or methods in an embodiment described herein, which when combined with parameters that assign sensor, time window and notification values to the activity primitive, an activity instance may be defined and included as part of a larger activity plan. Administrators of the activity plan can remove, modify parameters or add activity instances to the current activity plan. A designated primary caregiver can at any time upload the activity plan to the controller.

In some embodiments, time windows (in this document also referred to as time periods) may be defined as a block of time that begins with a start time and ends with an end time. Time windows may be managed by a scheduler. Time windows may serve at least two roles.

A first role served by time window may be as the maximum duration of time permitted between the actuation of an initiation sensor and the actuation of a second sensor paired to the initiation sensor, referred to as the completion (completes the time window) sensor. The time in between is referred to as a dynamic time window, generated at the time the initiation sensor actuates. Multiple time windows can exist simultaneously. Completion sensors that become active during the activity time window is the expected behavior. When completion sensors fail to actuate within the dynamic time window, the application may recognize the behavior as an exception. Normal and exception behaviors determine when the notification subsystem is activated. While an activity time window is active, the notification system remains dormant. If the completion sensor is actuated within the time window, the notification system will reset the time window to inactive and no notifications are generated for delivery to interested observers. If an exception occurs, indicating that the time window has expired, the notification system is activated.

A second role served by time windows may be for limiting the activity instance to within specified start and end times, referred to as enabling or static time windows. There are no limitations to time durations. If a static time window is defined in an activity instance, notifications associated with that activity can only be delivered during the static time window's start and end dates.

In some embodiments, activity primitives may support time windows that expect periods of no activity, where human activity is permitted to be quiescent while the person under sensor monitoring is still on the premise. Quiescent activity may have a maximum grace period (dynamic time window) encapsulated in a static time window.

In some embodiments, an action type may be associated with each instance of an activity primitive within the activity plan. An action type may specify a notification or other action to be performed when an activity associated with an activity primitive is detected. Notification types may carry a classification of either a) Informational (I) or b) Warning-ToCritical (WTC) and c) Action (A). Informational notifications from the perspective of the application carry no sense of urgency relative to time. Any activity instance can support any action type. The activity plan administrator may set the action type.

"Informational" notifications may offer the activity administrator a means of receiving a notification the moment a sensor is actuated without activating the notification system's WarningToCritical escalation processes. Activity primitives that do not have a dynamic time window (the NOW primitives) associated with them default to informational action types. The WarningToCritical classification may carry a sense of time urgency to the application and its time component may be proportional to the dynamic or static time window associated with that activity instance.

WarningToCritcal may signifiy to the activity administrator a method to first warn notification receivers (usually assigned caregivers/care partners) and other observers that an exception activity (undesirable activity) has occurred and requires caregiver/care partner attention or response to the warning. For WarningToCritical purposes, the alert color property is assigned in the notification data to signify the initial warning state. After a set of time proportional to the assigned time window size, if no response occurs from any member of the group of notification observers (notification endpoint receivers) the WARNING state progresses to a CRITICAL state with a designated alert color property assigned in the notification data.

Application notification resets may occur along with exception activity clear if the completion sensor actuates while the notification state's alert color is warning. If actuation occurs when the notification state's alert color is critical then the application will not reset, exception status remains, requiring the notification observers to manually reset the notification system from the exception to normal status. Alert color in normal status is now set to informational.

Action types may denote an action that will be performed as an instruction from the application server to the controller on premise to perform an action on a premise sensor. An exemplary action type would be to turn on a light switch or release a door lock.

The notification and status scheme described above may be expanded to include other stimuli including hut not limited to sound, haptic, etc.

FIG. 1 is a schematic diagram illustrating a virtual care/monitoring system 100, according to some embodiments. A monitoring system configured to identify movement and status (location, time duration in a location, direction of movement, last activity) of an inhabitant or occupant of a premises, the system, comprised of but not limited to a webserver, application server, a host computer connected using internet protocols, receives from at least one controller at the premise notifications based on sensor data captured at the premises indicating human physical motion consistent with or in conflict with an activity plan.

In the illustrated example, a single premise is shown for simplicity, but it should be appreciated that a system may support multiple customers and therefore many premises. The system is comprised of connected sensors that bi-directionally communicate and relay status to a controller 101 which in turn communicates with processes on a remote server residing in the cloud services 102. Cloud services 102 provides the mechanism to integrate any outside entity 103. Outside entities can be devices, processes, or systems that can send and receive data. The most common entity will be people with mobile devices. While the primary function of the controller 101 is to manage the bi-directional communications of data to/from the sensors, some controllers may support the ability to be programmed to process sensor data as well. This system can work with controller that support either configuration and with controllers that support any network topology (e.g. mesh, wifi, etc.) or protocol (e.g. z-wave, zigbee, etc.). In addition to the sensors shown (motion, contact, and temperature), any sensor that supports bi-directional communication of data can be used. User information, configuration, notification arc supported on the remote server through a variety of interfaces to support desktop, mobile, tablets, etc.

In accordance with some embodiments, the processes on the remote server may receive user input from which an activity plan is constructed. The activity plan may be transferred to the controller, which may process sensor outputs and generate messages and/or alerts in response to the sensor outputs.

FIGS. 2-8 below are flowcharts that show how activities (or movements) are modelled using sensor data, time windows, and notifications (explained in connection with FIGS. 9-11) using different processes (or activity primitives) associated with different types of activities. Seven (7) activity primitives are illustrated in the following examples. However, it should be appreciated that the present application is not limited to seven primitives. Additional configurations could be created that use different configurations of inputs based on sensors, time windows, and notifications (or alerts). The illustrated seven activity primitives model the movements of common daily activities as well as support several of what health professionals refer to as the "activities of daily living" (ADLs), the routine activities that people tend do every day without assistance. Inputs to the primitives may be created by an administrator, for example, as illustrated shown in FIG. 12B. One or more activity may be modelled, which may form an Activity Plan when combined, for example, as illustrated in FIGS. 12A-12B. A data store may comprise an activity plan comprising a plurality of primitives that define a model activity pattern for the inhabitant of the premise. The data store for the activity plan may exist in the controller and/or the application server. Synchronization of the activity plan may include a push from the application server to the controller. The updates can be in part or in whole. An update may also include a consistency check between the application and controller activity plans existing in the data stores of each device.

The following discussion may employ at least one non-transitory computer-readable medium, wherein the plurality of sensors comprises a first sensor and a second sensor; and an activity primitive of the plurality of activity primitives indicates an activity based on the first sensor indicating an occupant of the premises moving past or opening a contact device defined as the first sensor and the second sensor defined as moving past or opening a contact device indicating the occupant of the premises actuating a second sensor within a time window specified by the activity primitive.

Figure 2:
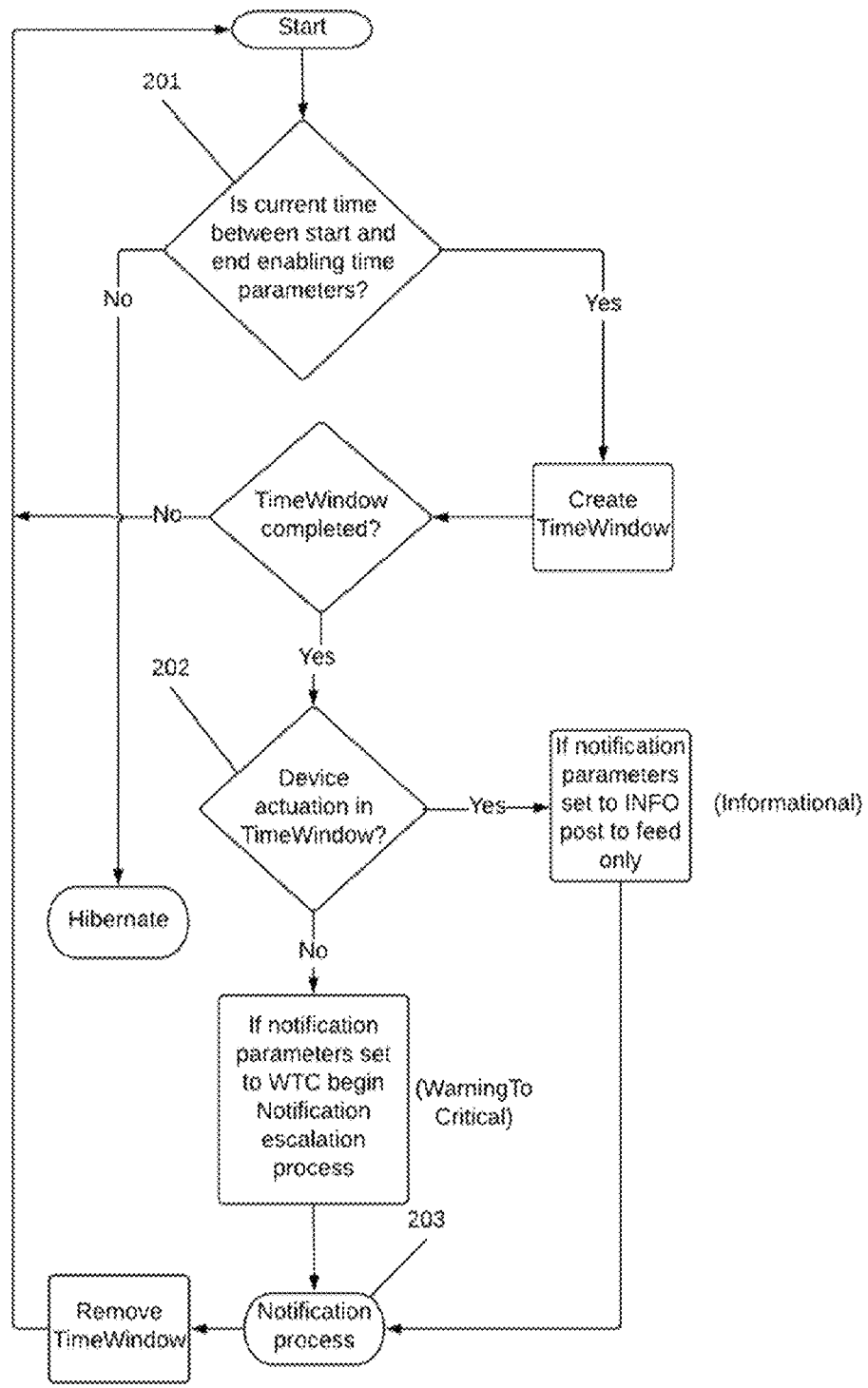
FIG. 2 is a flowchart, illustrating an activity primitive comprising processing to check for sensor events during a time window of the activity primitive and/or at the end of the time window (premiseActivity primitive), according to some embodiments.

FIG. 2 is a flowchart, illustrating an activity primitive comprising processing to check for sensor events during a time window of the activity primitive and/or at the end of the time window (premiseActivity primitive), according to some embodiments.

The premiseActivity primitive is enabled (act 201) between start time and end time parameters of the enabling window time. Event processing invoked at completion of time windows (act 202) and will check for sensor events (motion, contact, temp, moisture sensors) during the time window at the end of a time window (TimeWindow). Notification containing event status (act 203) is sent at the end of the time window (e.g., did mom enter the kitchen by 9 am). Completion sensors actuated during an active time window are regarded as an expected behavior. If no completion sensors were actuated it can be regarded as unexpected behavior.

Figure 3:
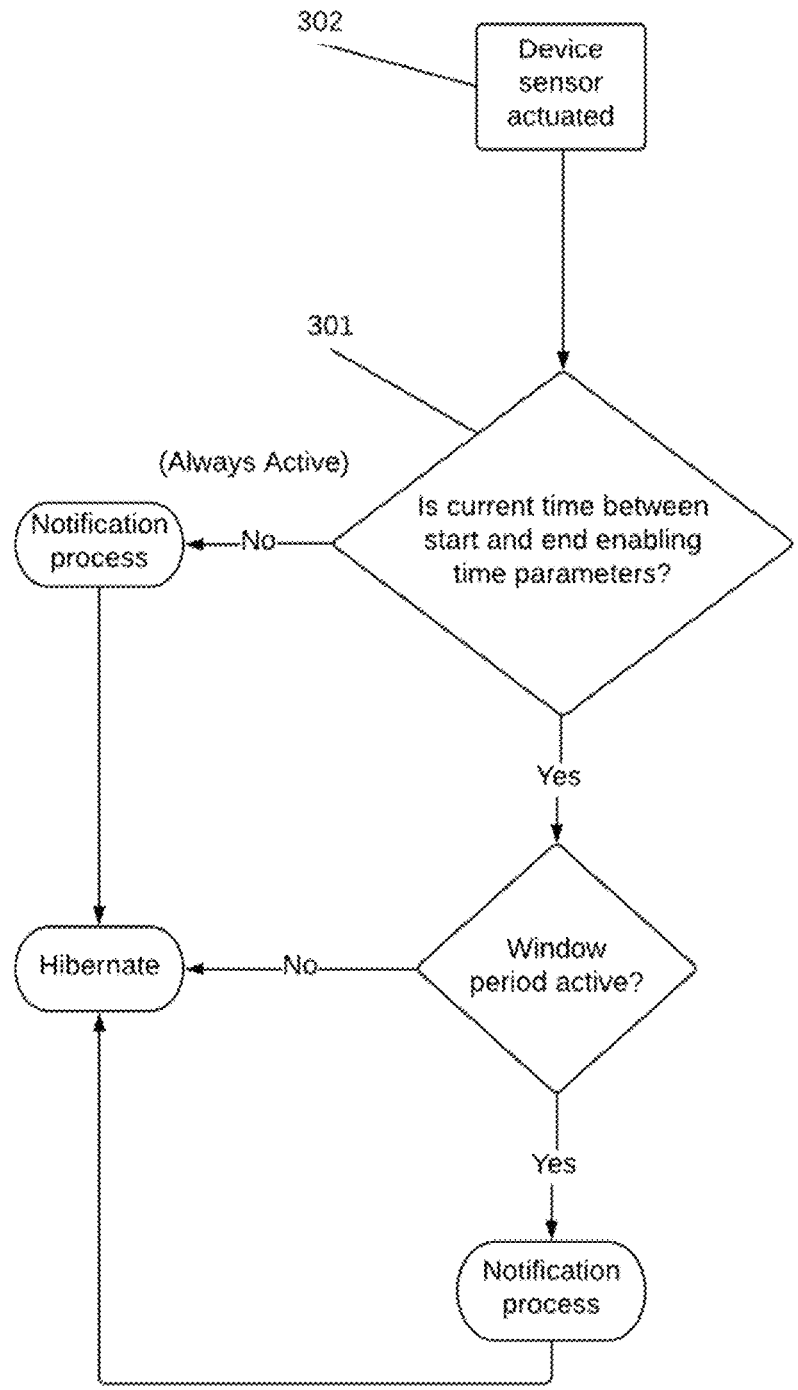
FIG. 3 is a flowchart, illustrating an activity primitive indicating real-time transmission of a notification in response to a sensor output that indicates an event during the time window of the activity primitive (premiseActivityNow primitive), according to some embodiments.

FIG. 3 is a flowchart, illustrating an activity primitive indicating real-time transmission of a notification in response to a sensor output that indicates an event during the time window of the activity primitive (premiseActivityNow primitive), according to some embodiments.

The premiseActivityNow primitive can be active all the time or limited to enabling time (act 301) windows (time windows that limit sensor event processing to only times that occur between the start and end time of the enabling time window). The process will check for sensor events (motion, contact, and temp sensors) initiating an immediate notification if activated (act 302). Events can occur anytime (24 hour time window) or within a defined static time window.

Figure 4:
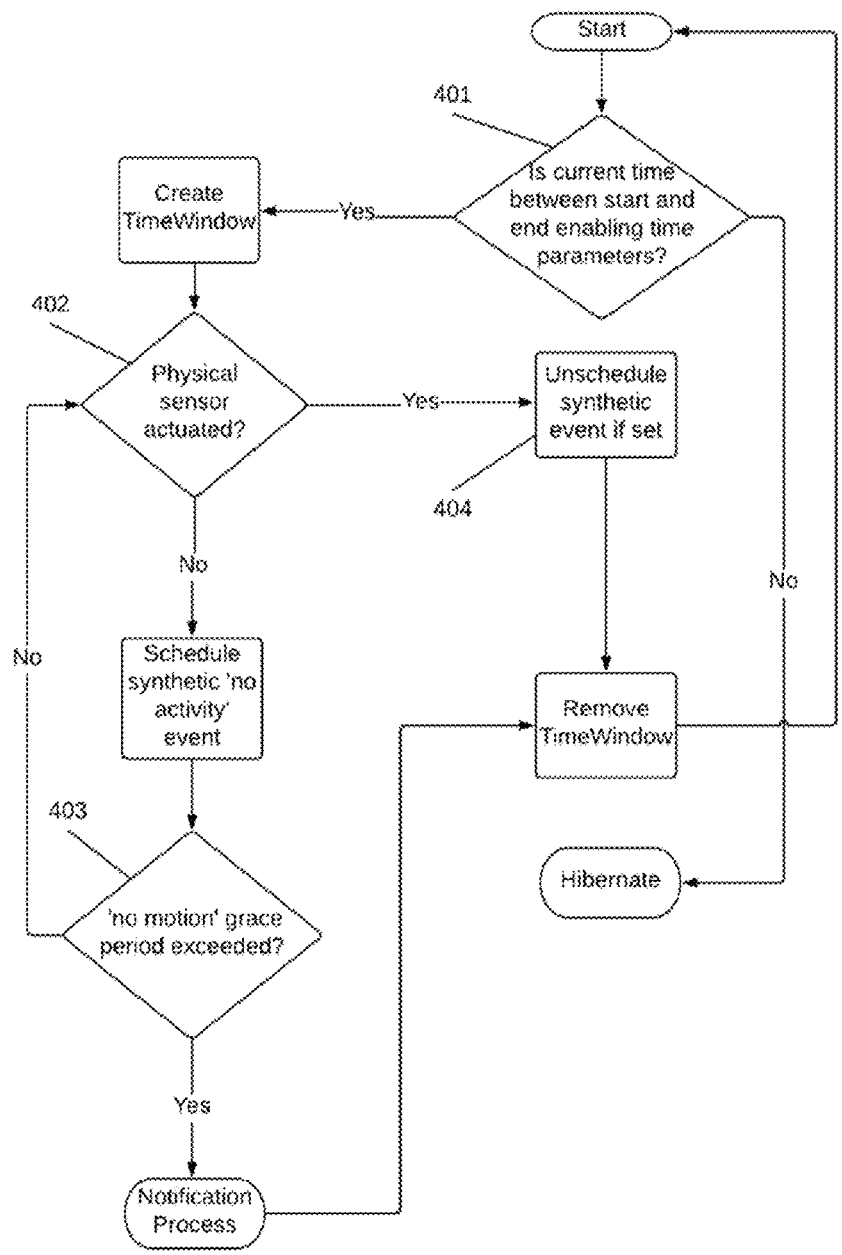
FIG. 4 is a flowchart, illustrating an activity primitive indicating processing to check for absence of sensor events during a time window plus a grace period following the end of the time window (premiseNoActivity primitive), according to some embodiments.

FIG. 4 is a flowchart, illustrating an activity primitive indicating processing to check for absence of sensor events during a time window plus a grace period following the end of the time window (premiseNoActivity primitive), according to some embodiments.

The premiseNoActivity primitive is enabled (act 401) between the start and end time parameters of the enabling time window and is invoked on regular intervals and will check for absence of sensor events (act 402) (i.e. no motion or contact open/close events within premise or a specific sensor) during a time window. Events can extend past a defined grace period (act 403) established by the time window. Notifications are sent at the end of the grace period. Thus grace periods are defined through time start and end time markers where no sensor activity is detected in the time period between the markers. These periods of no sensor activity is considered acceptable behavior to the observer on the part of the inhabitant. If a physical sensor is detected (act 404), the window is removed and restarts again if the current time is between the enabling start and end times.

Figure 5:
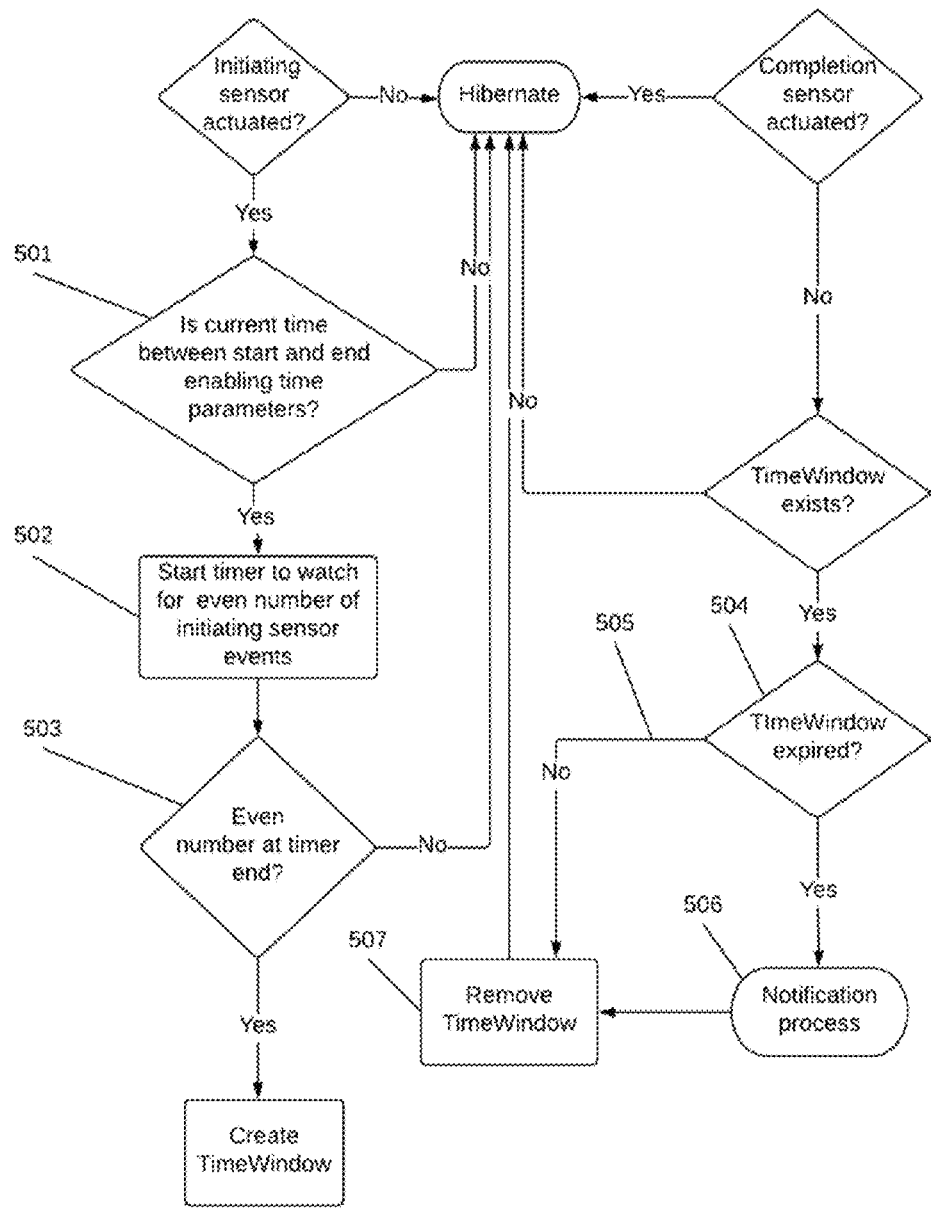
FIG. 5 is a flowchart, illustrating an activity primitive that delays time window creation until a first sensor indicates an even number of total first events within more than one sampling cycles of the controller and a second sensor does not indicate a second event within the time window associated with the activity primitive (sequencedActivity primitive), according to some embodiments.

FIG. 5 is a flowchart, illustrating an activity primitive that delays time window creation until a first sensor indicates an even number of total first events within more than one sampling cycles of the controller and a second sensor does not indicate a second event within the time window associated with the activity primitive (sequencedActivity primitive), according to some embodiments.

The sequencedActivity primitive is enabled (act 501) between the start and end time parameters of the enabling time window and may be invoked at regular intervals. The primitive will check for an unexpected but planned sensor event (involving specific sensor pairs defined as the initiating sensor and the completion sensor) that creates a dynamic time window which is removed when the completion sensor is activated. This primitive generates a notification if the completion sensor is not activated by the time the created time window expires (act 504) (e.g. a bathroom exit). The completion sensor (defined in the activity plan) is monitored once the time window (TimeWindow) is created. Sequenced activity does not create the time window (TimeWindow) at first actuation of the initiating sensor. Time window creation does not occur until either an even number (act 502) of sensor events occurs within, for example, a two minute timer, or more than one first event sampling cycle. If the initiating sensor event total since the first actuation of the initiating sensor is an even number (act 503) at the end of the timer, then the room is considered habituated. If the event total is odd (act 507), then the room is considered not habituated long enough to create a time window (TimeWindow). After 2 cycled loops in the controller, the event total is summarized and window creation determine by the even or odd event total. If time window is created, the completion sensor is monitored for actuation. In this case, an actuated completion sensor will (act 505) shutdown the primitive since the completion sensor resides outside the room that has the limited habitation time assigned to it. If the completion sensor is not actuated (act 506), normal time window expiration (the TimeWindow) occurs which is terminated and the notifier given notice.

Figure 6:
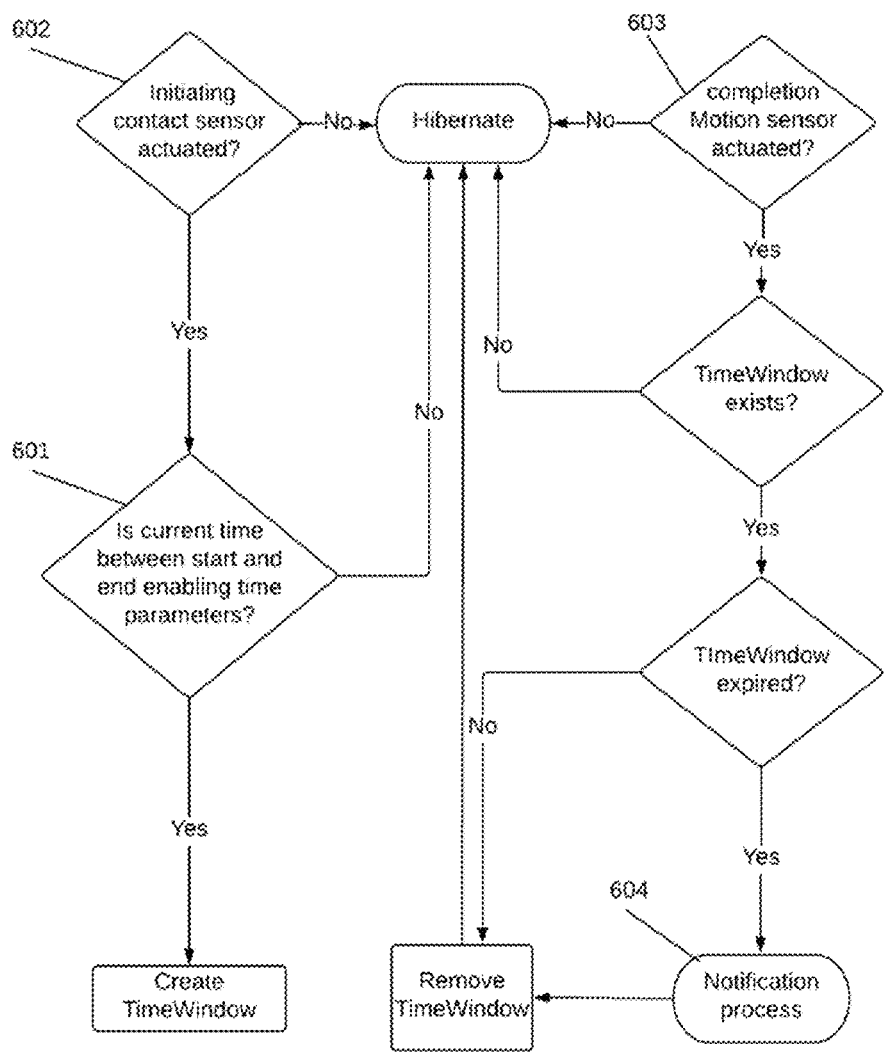
FIG. 6 is a flowchart, illustrating an activity primitive indicating transmitting a notification when a first sensor indicates a first event and a second sensor does not indicate a second event within the time window associated with the activity primitive following the first event (contactMotion primitive), according to some embodiments.

FIG. 6 is a flowchart, illustrating an activity primitive indicating transmitting a notification when a first sensor indicates a first event and a second sensor does not indicate a second event within the time window associated with the activity primitive following the first event (contactMotion primitive), according to some embodiments.

The contactMotion primitive is enabled between the start and end time parameters of the enabling time window (act 601) and will check an unexpected but planned actuation of a specific contact sensor (act 602) that is mapped or assigned to a specific motion sensor. This mapping assignment creates a dynamic time window when the contact sensor is actuated and is removed when the paired motion sensor, i.e. completion sensor, is actuated within the designated time window (act 603). Notification is not sent if the motion is detected within the time window. A notification is generated if motion falls outside the time window or motion never occurs (act 604).

Figure 7:
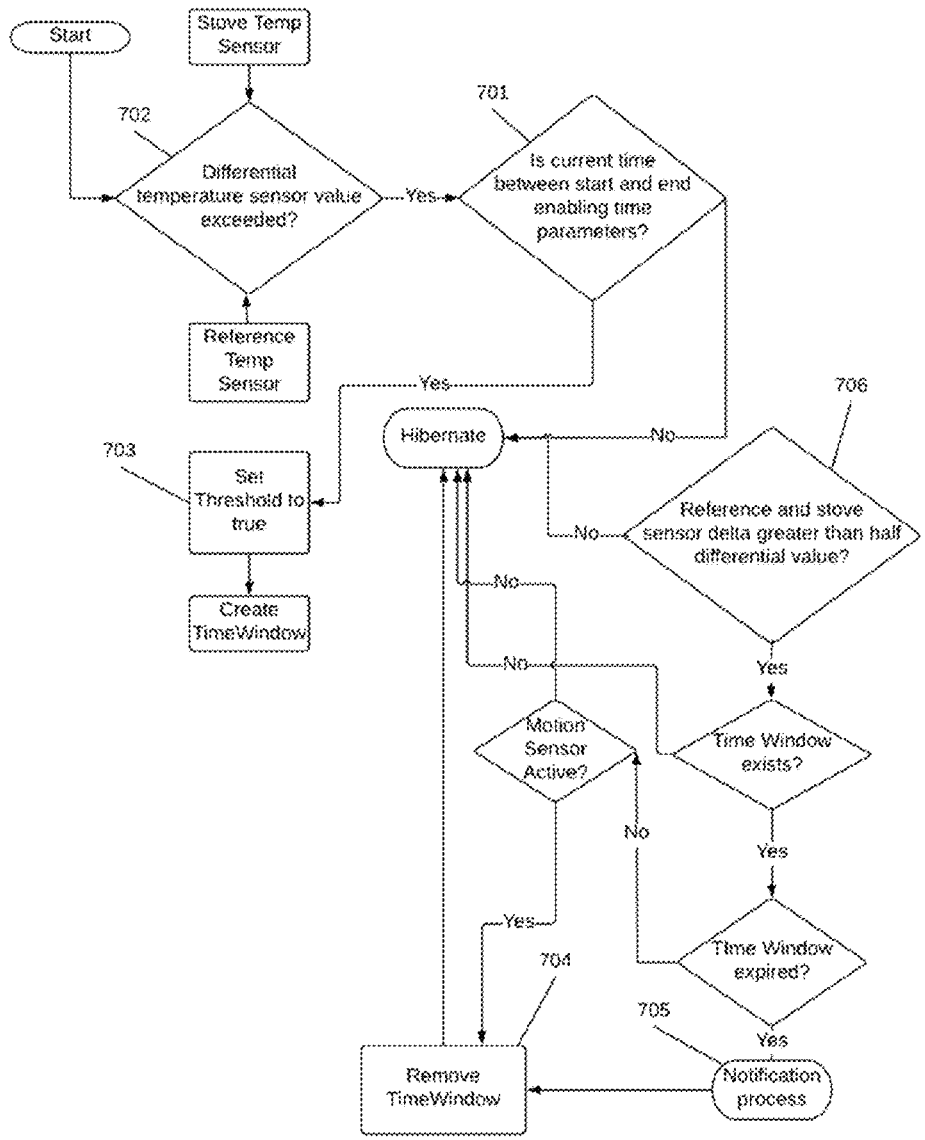
FIG. 7 is a flowchart, illustrating an activity primitive an activity primitive indicating transmitting a notification when a first sensor indicates a first event and a second sensor does not indicate a second event within the time window associated with the activity primitive following the first event (tempMotion primitive), according to some embodiments.

FIG. 7 is a flowchart, illustrating an activity primitive an activity primitive indicating transmitting a notification when a first sensor indicates a first event and a second sensor does not indicate a second event within the time window associated with the activity primitive following the first event (tempMotion primitive), according to some embodiments.

The tempMotion primitive is enabled between the start and end time parameters of the enabling time window (act 701) and will check an unexpected but planned actuation of a specific temperature sensor ("STOVE" temp sensor) against a reference room temperature sensor ("KITCHEN" temp sensor) (act 702). If the temperature difference between the two sensors is greater than an assigned threshold value then a time window (the TimeWindow) is created and a specific motion sensor is monitored for activity (act 703). If the motion sensor is actuated in the time window then the time window (TimeWindow) is destroyed and restarted (act 704). Notification is not sent is the motion is detected within the time window. A notification is generated if motion falls outside the time window or motion never occurs during the active time window (TimeWindow) (act 705). If the time window never expires and the temperature difference between 'STOVE' temp sensor and 'KITCHEN' falls below one half the temperature difference then the time window (TimeWindow) is destroyed (act 706). That is mapped or assigned to a specific motion sensor. This mapping assignment creates a dynamic time window when the temperature is actuated and is removed when the paired motion sensor is actuated within the designated time window. Notification is not sent if the motion is detected within the time window. A notification is generated if motion falls outside the time window or motion never occurs.

Figure 8:
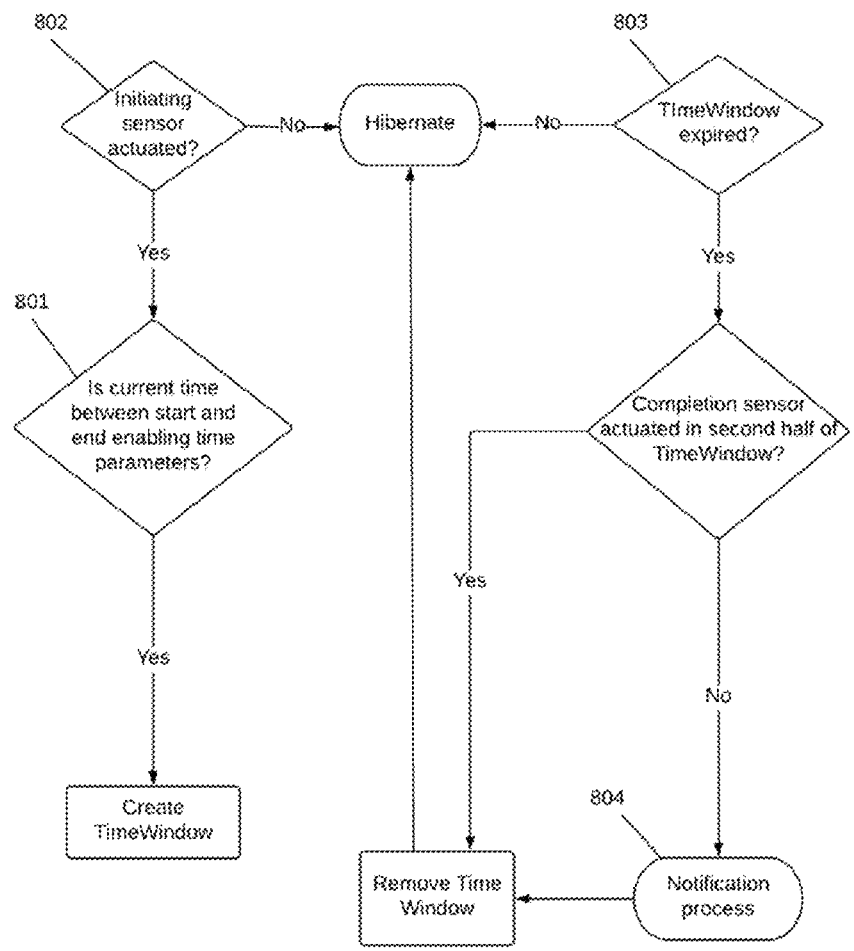
FIG. 8 is a flowchart, illustrating an activity primitive an activity primitive indicating transmitting a notification when a first sensor indicates a first event and a second sensor does not indicate a second event within the time window associated with the activity primitive following the first event (motionMotion primitive), according to some embodiments.

FIG. 8 is a flowchart, illustrating an activity primitive an activity primitive indicating transmitting a notification when a first sensor indicates a first event and a second sensor does not indicate a second event within the time window associated with the activity primitive following the first event (motionMotion primitive), according to some embodiments.

The motionMotion primitive is enabled between the start and end time parameters of the enabling time window (act 801) and will check an unexpected but planned actuation of a specific motion sensor that is mapped or assigned to another specific motion sensor. This mapping assignment creates a time window (TimeWindow) when the first motion sensor is actuated (act 802) and is removed when the paired motion sensor is actuated within the designated time window (act 803). Notification is not sent if the motion is detected within the time window. A notification is generated if motion falls outside the time window or motion never occurs (act 804).

Figure 9:
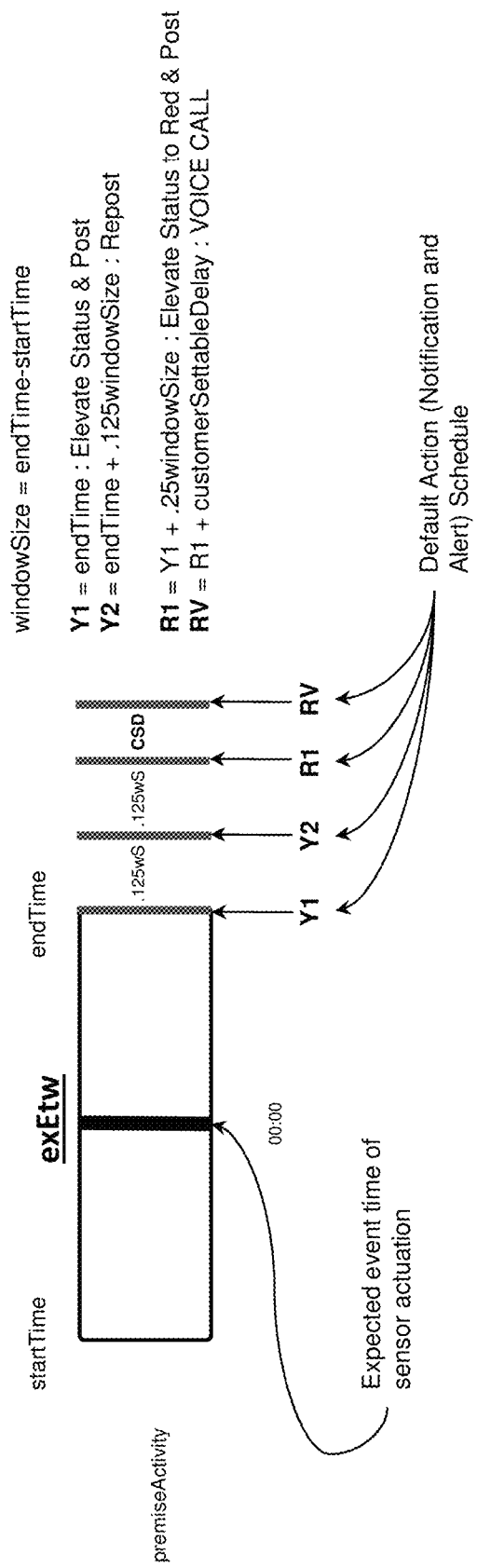
FIG. 9 is a schematic diagram illustrating an Expected Time Event Window timeline that shows the relationship between expected events, time, and notifications, according to some embodiments.

FIG. 9 is a schematic diagram illustrating an Expected Time Event Window timeline that shows the relationship between expected events, time, and notifications, according to some embodiments. An Expected Time Event Window (exEtw) may be associated with an event that is expected to occur. For example, if a person starts their day approximately the same time every day then this time window could be used to model the expected event. This is an expected event in an expected time window. The time window embodies a timeline that establishes a relationship between expected events (sensor actuation), time, and notifications. An Expected Time Window has known start and end times and is used to determine if the expected event (sensor actuation) occurred within the time window. The absence of the expected event within the time window can be is interpreted as an exception to an expected movement pattern. Notifications and alerts would be issued as per the default framework described as follows. The total duration of time between the start time and end time create a window size that's used to determine the first notification alert (Y1), the second notification alert (Y2), the third notification alert (R1) and the fourth notification alert (RV) voice call or other notification (IFTTT). The exact time of Y2, R1, and RV are all derived from the start of the event and the event duration. However, these times could be adjusted to any pattern or be completely and customized independent of the window size.

Figure 10:
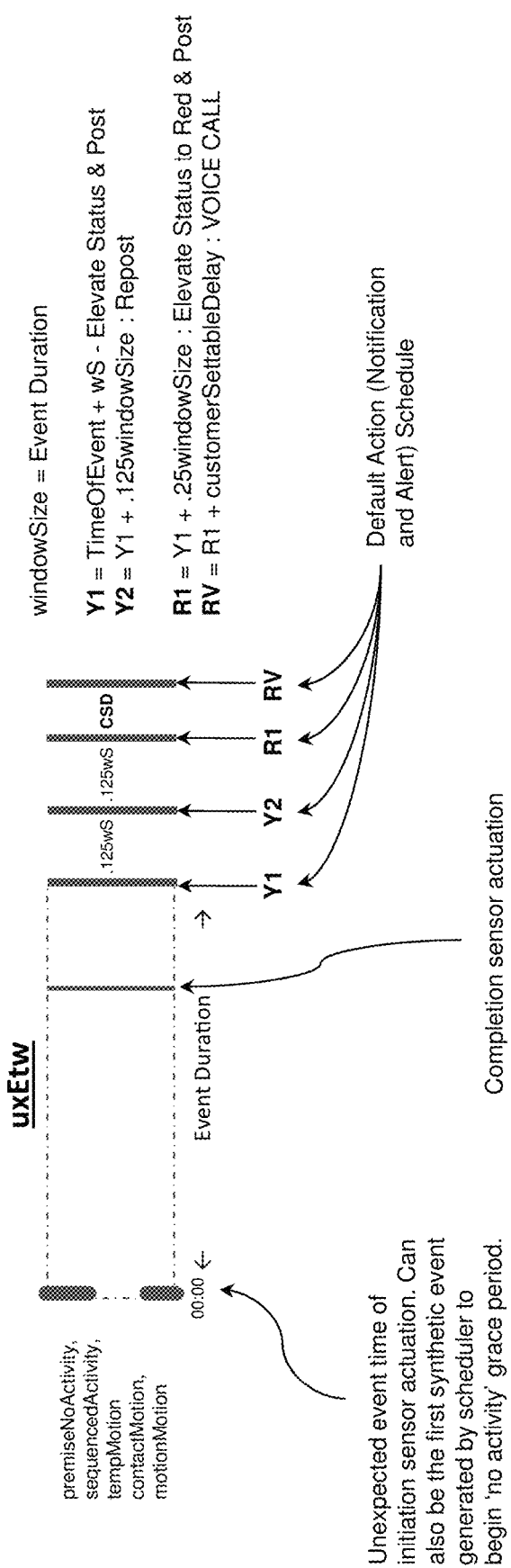
FIG. 10 is a schematic diagram illustrating an Unexpected Time Event Window timeline that shows the relationship between unexpected events, time, and notifications, according to some embodiments.

FIG. 10 is a schematic diagram illustrating an Unexpected Time Event Window timeline that shows the relationship between unexpected events, time, and notifications, according to some embodiments. An Unexpected Time Event Window (uxEtw) may be associated with an unexpected event. It is a timeline that establishes relationship between unexpected events, time, and notifications. For example a person goes to the bathroom. It's unexpected because we don't know when the event will occur. UnExpected Event Time Window is a time window without a known start and end time. The start of the time window is established when the event is detected. The absence of a completion sensor actuation can be interpreted as an exception. Notifications and alerts would be issued as per the default framework described as follows. An event duration is specified for this time window. The start time plus the event duration is used to determine the first notification alert (Y1), the second notification alert (Y2), the third notification alert (R1) and the fourth notification alert (RV) voice call or other notification (IFTTT). The exact time of Y2, R1, and RV are all derived from the start of the event and the event duration. However, these times could be adjusted to any pattern or be completely customized independent of the window size.

Figure 11:
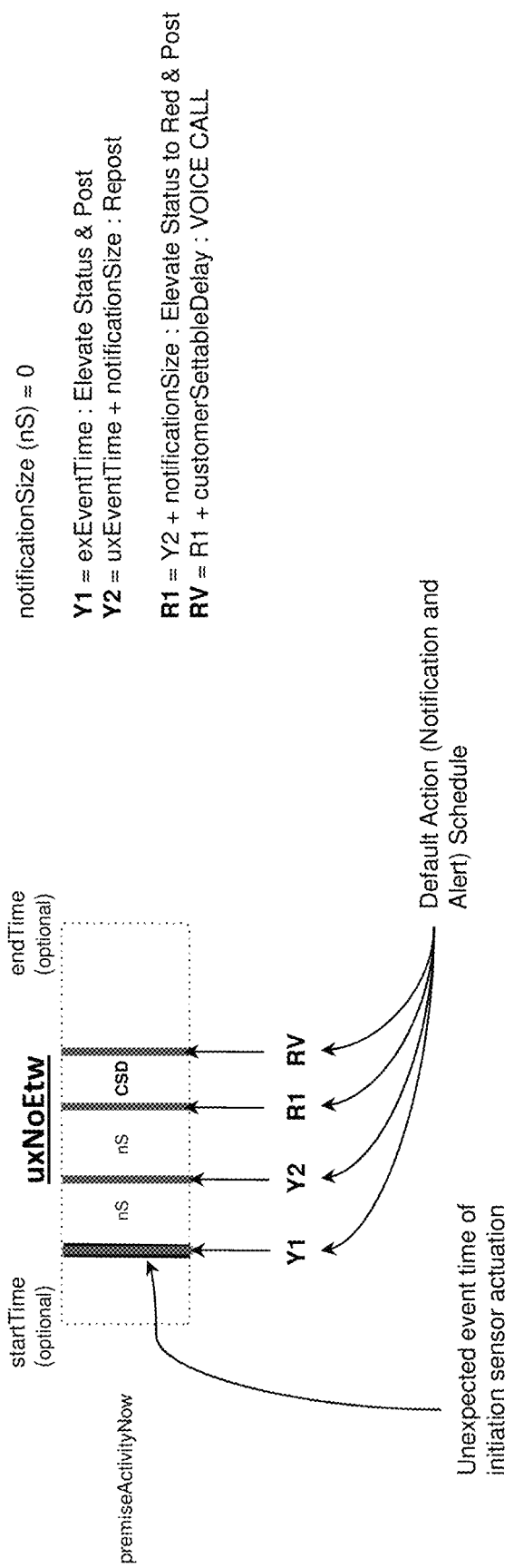
FIG. 11 is a schematic diagram illustrating an Unexpected NoTime Event Window timeline that shows the relationship between unexpected events that can occur at any time and notifications, according to some embodiments.
Figure 12B:
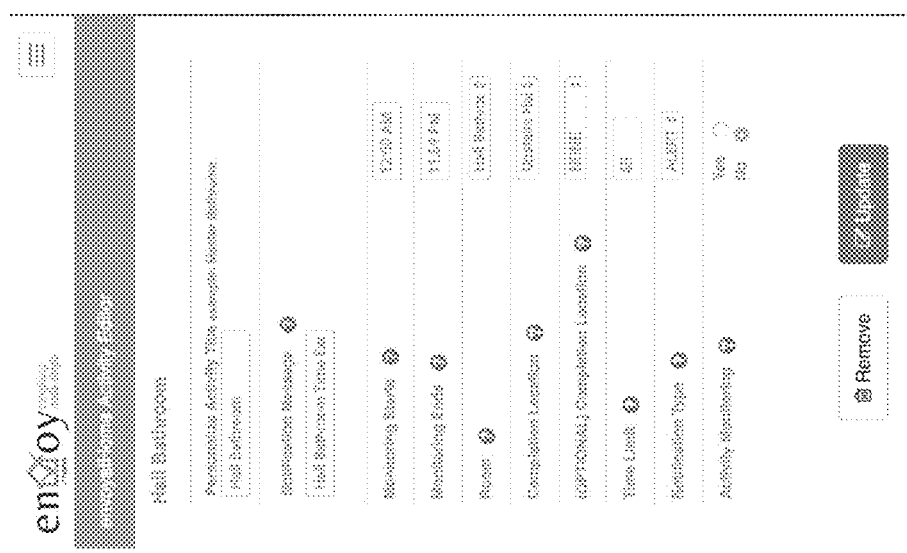
FIG. 12B is a schematic diagram illustrating a Sample Data Entry, using the Activity Editor by an Administrator, according to some embodiments.

FIG. 11 is a schematic diagram illustrating an Unexpected NoTime Event Window timeline that shows the relationship between unexpected events that can occur at any time and notifications, according to some embodiments. An Unexpected NoTime Event Window (uxEtw) may be associated with an unexpected event. This time window has no duration and can immediately trigger a notification. For example, a person entering a restricted room may trigger an immediate notification. A start and end time can be used to establish a time frame for monitoring. Since there is no event duration per se, a notification window size (or simply notification size) is specified as a notification size. The purpose of this event time window is to support immediate notification of an event. The total duration of time between the start of the event and the notification size is used to determine the first notification alert (Y1), the second notification alert (Y2), the third notification alert (R1) and the fourth notification alert (RV) voice call or other notification (IFTTT). The exact time of Y2, R1, and RV are all derived from the start of the event and the notification size. However, these times could be adjusted to any pattern or be completely and customized independent of the window size.

The application server may be configured to present a user interface through which the action plan is specified by a user a series of primitives, each reflecting an event and a time window. FIG. 12A is a schematic diagram illustrating a Sample Activity Plan, showing the Implementation of the Activity Primitives with supporting Time and Notification Parameters, according to some embodiments.

In the illustrated example, an activity plan is specified as a sequence of primitives, with parameters associated with the primitives. The activity plan may be specified directly by a user in this tabular form. The computer system receiving and configuring a controller based on the activity plan may maintain data about this activity form in a data structure that preserves the illustrated relationship between primitives and their parameters. However, the manner in which the activity plan is created is not a limitation on the invention. For example the activity plan may be created by user inputs through a graphical user interface. Using known GUI programming techniques, the computer system may prompt the user to specify information as reflected in the tabular activity plan of FIG. 12, such as by prompting a user to select a primitive, specify a time window associated with the primitive, if any; specify a sensor or sensors; and/or specify one or more notifications or other actions, and timing information (such as grace periods, escalation times, etc.) associated with those events or notifications.

In the example illustrated in FIG. 12A, each row of the table is referenced as either an activity instance or activity definition. FIG. 12A shows ten activity instances in the activity plan. Act 1201 is the Activity number and acts as an index for referencing the individual instances. Act 1202 shows the seven activity primitives. The seven activity types are:

1. premiseActivity—(FIG. 2) Results of sensor actuation are not examined and notifications are not delivered until the end of the static time window. DeviceScopeType definitions reference in act 1203 and 1213 are the same as described in activity primitive PremiseActivityNow. Act 1209 and 1212 reference the default action types of Informational (I) or WarningToCritical (WTC) or Action (A) assigned to all primitives. The activity administrator can define the action type at activity instance creation (See FIG. 12B).
2. premiseActivityNow—Sensor events initiating an immediate response to event observers with a notification sent from the monitoring system to the notification receivers. Can occur anytime and does not require a defined time window to be active and works without sensor pairing. The DeviceScopeType referenced in act 1203 (device inclusion) can be either a) single sensor, b) sensors of a particular activation type within a premise, or all sensors of all activation types within a premise. Examples of a particular activation type within a premise would be all motion sensors, all open/close contact sensors, all temperature sensors, all moisture sensors that are registered with and sending event data to the premise controller. All sensors in the premise would include all sensor types registered and sending event data to the controller.
3. premiseNoActivity—this activity primitive comprises a 'no activity' primitive; and selectively sending a message when no activity is detected for a period of time specified in connection with the activity primitive. Looking for no activity (e.g., no motion or contact open/close events within premise or by a specific sensor). Can extend past the grace period within a time window. Notification is sent at the end of the grace period. This activity requires the time window size be configured by the activity administrator and is referred to as the grace period. Grace periods can be defined for an entire day or encapsulated within a static time window. Notifications are sent if no activity (no sensors are actuated) is extended beyond the grace period, e.g., dad napping during the day (time window) so a grace period longer than the normal grace period over the remaining hours.
4. sequencedActivity—An unexpected initiating sensor event that creates a time window which is removed when the completion sensor is activated. This activity type generates a notification if the completion sensor is not activated by the time the created time window expires (e.g. a bathroom exit). The completion sensor is defined as being the immediate sensor actuated (i.e. hallway motion sensor to the bathroom) just prior to the initiating sensor's actuation (i.e. bathroom motion sensor activated during bathroom entrance activity). This is referenced in act 1210 as flex pairing. Act 1211 references the dynamic time window creation with the TimeWinSize set by the activity administrator.
5. contactMotion—An unexpected actuation of a specific contact sensor that is mapped or assigned to a specific motion sensor or a group of sensors. Act 1214 highlights the pairing with a deviceScopeType of 'paired'. This mapping assignment creates, similar to act 1211, a dynamic time window when the contact sensor is actuated and is removed when the paired motion sensor is actuated within the designated time window. Notification is not sent if the motion is detected within the time window. A notification is generated if motion falls outside the time window or motion never occurs. Act 1215 uses the example of a premise exit door acting as the initiating contact sensor followed by completing motion sensor or sensors to determine if the human activity was to leave the premise because no completing motion sensor or sensors was detected after the contact sensor was actuated.
6. tempMotion—An unexpected actuation of a specific temperature sensor that is mapped or assigned to a specific motion sensor or a group of motion sensors. Act 1214 highlights the pairing with a deviceScopeType of 'paired'. This mapping assignment creates a dynamic time window, similar to act 1211 when the temperature sensor is actuated and is removed when the paired motion sensor is actuated within the designated time window. Notification is not sent if the motion is detected within the time window. A notification is generated if motion falls outside the time window or motion never occurs.
7. motionMotion—An unexpected actuation of a specific motion sensor that is mapped or assigned to another specific motion sensor or a group of sensors. Act 1214 highlights the pairing with a deviceScopeType of 'paired'. This mapping assignment creates a dynamic time window, similar to act 1211, when the first motion sensor is actuated and is removed when the paired motion sensor is actuated within the designated time window. Notification is not sent if the motion is detected within the time window. A notification is generated if motion falls outside the time window or motion never occurs.

FIG. 12B is a schematic diagram illustrating a Sample Data Entry, using the Activity Editor by an Administrator, according to some embodiments. The activity editor may be used to configure individual items of an activity plan (Activity Planner). In this example, the activity presents a graphical interface window to the user, with fields corresponding to information to be entered to specify the activity.

Figure 13:
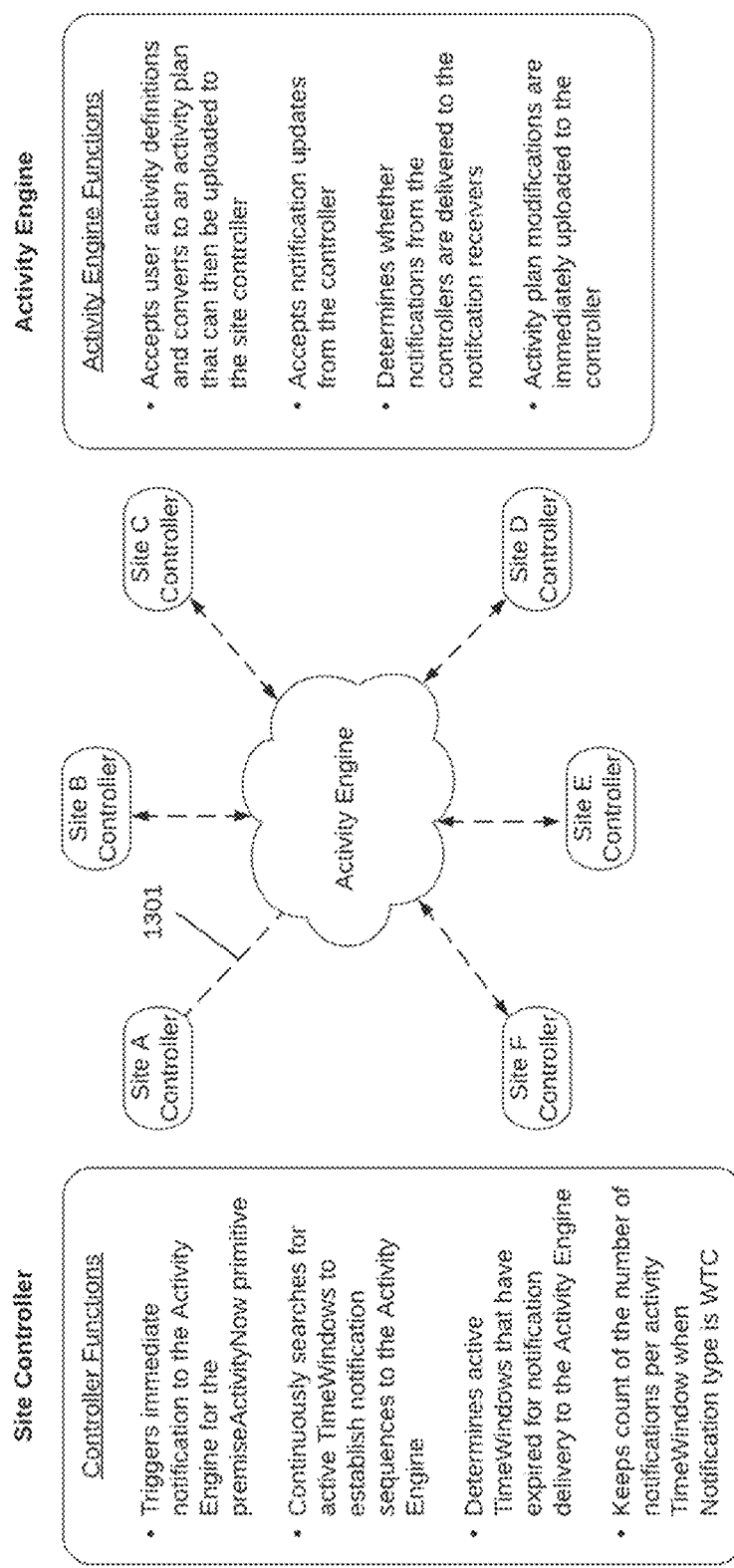
FIG. 13 is a schematic diagram illustrating functional interaction between Site Controller and Activity Engine, according to some embodiments.

FIG. 13 is a schematic diagram illustrating functional interaction between Site Controller and Activity Engine, according to some embodiments. Once an activity plan is created (or modified) the activity plan is deployed to a controller that executes the activity plan.

The controller located on premise may be a computer readable medium comprising computer executable instructions that, when executed by at least one processor in a controller coupled to a plurality of sensors at a premise, performs a method of monitoring activity of a human within a premises, the method comprising: receiving over a network a plurality of activity primitives, each action primitive comprising: an enabling time window for all primitives, an initiating sensor (necessary for primitives with the window type of uxEtw), a completion sensor (necessary for primitives of type premiseActivity, sequencedActivity, contactMotion, motionMotion), a notification type of either INFORM, WARN, ALERT representing an indication of an activity detectable based on outputs of the plurality of sensors; based on the outputs of the plurality of sensors and the plurality of action primitives, communicating over the network notifications of occurrence of non-occurrence of activities associated with the plurality of activity primitives.

In some embodiments, the method may further comprise receiving over the network a command to add an activity primitive to the plurality of activity primitives.

In some embodiments, the method may further comprise receiving over the network a command to remove an activity primitive from the plurality of activity primitives.

In accordance with some embodiments, the controller may be a computing device programmed or configured to perform computations and interact with other devices to perform the actions required to generate notifications or take other actions in accordance with the activity plan. The controller, for example, may have sensor interfaces such that it can obtain sensor outputs. The controller may have one or more timers, such that it can track time and processing power to perform computations to determine whether the specified conditions associated with a primitive have been met. Additionally, the controller may have communication interfaces, such as a wireless network interface, such that it can receive an activity plan from an activity engine on a central server and communicate notifications.

Act 1301 shows a bidirectional relationship between the controller and the activity engine. The primary functions of the Activity Engine reflect its primary role of synchronizing activity plans between activity administrators and remote site controllers. Specific functions of the Activity Engine may include: Accepts user activity definitions and converts to an activity plan that can be synchronized and uploaded to the remote site (premise) controller; Accepts notification updates from the controller, converts data format for delivery to the receiver's data format; Determines if notifications from the controllers are delivered to the notification receivers based on preferences set by the receivers; Activity plan modifications are immediately uploaded to the controller's data store.

The site controllers may be unique within the architecture with each site controller representing one premise. A premise may be defined as a set of physical sensors that are registered and subscribed to a single controller. All sensor events may be reported and processed by the controller. Notifications may be determined at the controller. Specific controller functions may include: Triggers immediate notification to the Activity Engine for the premiseActivityNow primitive; Searches for active TimeWindows to establish notification requirements to the Activity Engine; Determines active TimeWindows that have timed-out for notification delivery to the Activity Engine; Keeps count of the number of notifications per activity TimeWindow when Notification type is WTC; Accepts and acknowledges success or failure of the Activity Plan updates as submitted by the Activity Engine.

Figure 14:
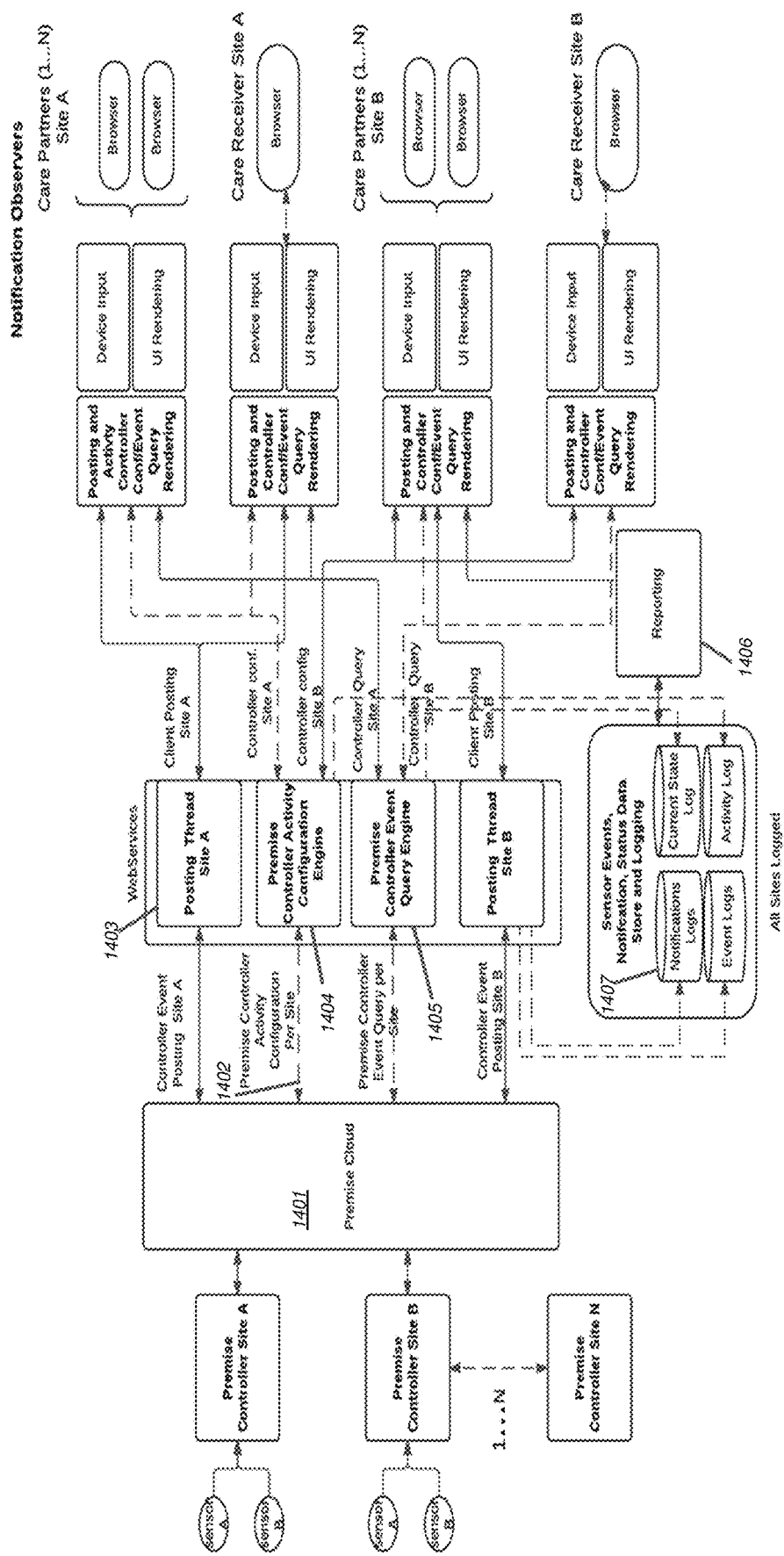
FIG. 14 is a schematic diagram illustrating Posting Thread, Active Engine, Event Query Engine in relation to sensor and user entry and exit points into the overall design, according to some embodiments.

FIG. 14 is a schematic diagram illustrating Posting Thread, Active Engine, Event Query Engine in relation to sensor and user entry and exit points into the overall design, according to some embodiments. A method of operating an alerting/notification system programmed with at least one activity primitive characterizing a potential activity of an occupant of a premises, the method may comprise: selectively sending at least one message to one or more notification observers of the alerting/notification system, in accordance with the activity primitive and the received sensor data; receiving data from a plurality of sensors; processing the received data to identify occurrence of an event associated by the activity primitive.

The activity plan may require adapting at least one criterion for selectively sending at least one message to one or more notification observers based on detecting when unexpected activity patterns appear.

Act 1401 references the premise cloud as a collection of premise controllers. Each controller is in separate locations and in constant bidirectional communications with physical sensors also resident within this same premise and assigned uniquely to that controller. As human movement occurs, physical sensors are actuated and the event recognized by the premise controller. The controller in turn examines the event and performs a lookup of the actuated device's deviceName. The deviceName is searched in the activity plan's deviceScope property. If the deviceName is matched in one or more activity instances with the proper TImeWinType (uxEtw), the controller creates one dynamic time window per activity instance.

The time window is terminated by either its paired completing sensor or the current time exceeds the time window's end time value. Processing for notification delivery begins if the time window expires without the completing sensor actuating within the time windows start and end date and time.

TimeWinTypes of exEtw and uxNoEtw do not generate dynamic time windows, defined as time windows initiated by an unexpected physical sensor event. The exEtw creates a static time window in anticipation of an expected physical or synthetic sensor event. As in the uxEtw TimeWinType, the notification occurs approximately at the time window expiration if the expected sensor event never occurs in the time window.

The premise cloud receives the incoming controller notification with the controller's unique identifier and sends the data to the webserver of the application. After the web server parses the controller Id highlighted in act 1403 the posting thread will post the notification to the proper thread matched to that specific controller ID.

Similar to the posting thread, the activity engine referenced in act 1404 attaches the controller ID to the activity data generated by the administrator for delivery of data to the premise cloud. Conversely, controller acknowledgements to the activity engine are tagged by the controller with its controller ID and parsed by the activity engine for delivery to the administrator making activity modifications. One of the functions of the Activity Engine is to query and update activity plans that may not be synchronized with the administrator's current recommendation (act 1402). Typically, in the event of a web service or network outage, activity plans resident in the controller will need to be synchronized for accuracy with the activity engine.

Act 1405 is the Query Engine. Its primary function is the collection of a) historical notification data, b) historical sensor status c) current alert status from the controller. The query engine, like the activity engine can collect from a single controller or a group of controllers for this data. The controller ID is used to route the request through the premise cloud and to the specific controller.

In summary, the controller's ID serves as the reference tag for routing data to and from web server applications, notification receivers (indirectly from the observed inhabitants mapping to the controller ID and a second mapping to the notification observers) to the target controller.

Act 1406 references the reporting capability of the application. The reporting function is gathers data from the database logs in act 1407 for reports requested by notification observers.

The database is a data store of current and historical events, notifications, logs. The data store is employed for analyzing the received data to identify trends in daily movement patterns (e.g. improving/declining health patterns of the inhabitant) over comparative time periods of historical activity.

Notification observers are registered to the system and can be anyone with access permission to be an observer. Access permission is authorized by the primary care giver. Notification observers can be comprised of third party services. Once registered, notification observers will receive data without human intervention. The application server will selectively send at least one message to one or more notification observers, sending a message to alarm companies, emergency medical, fire rescue, police and entities providing caregiver or care monitoring services.

Figure 15:
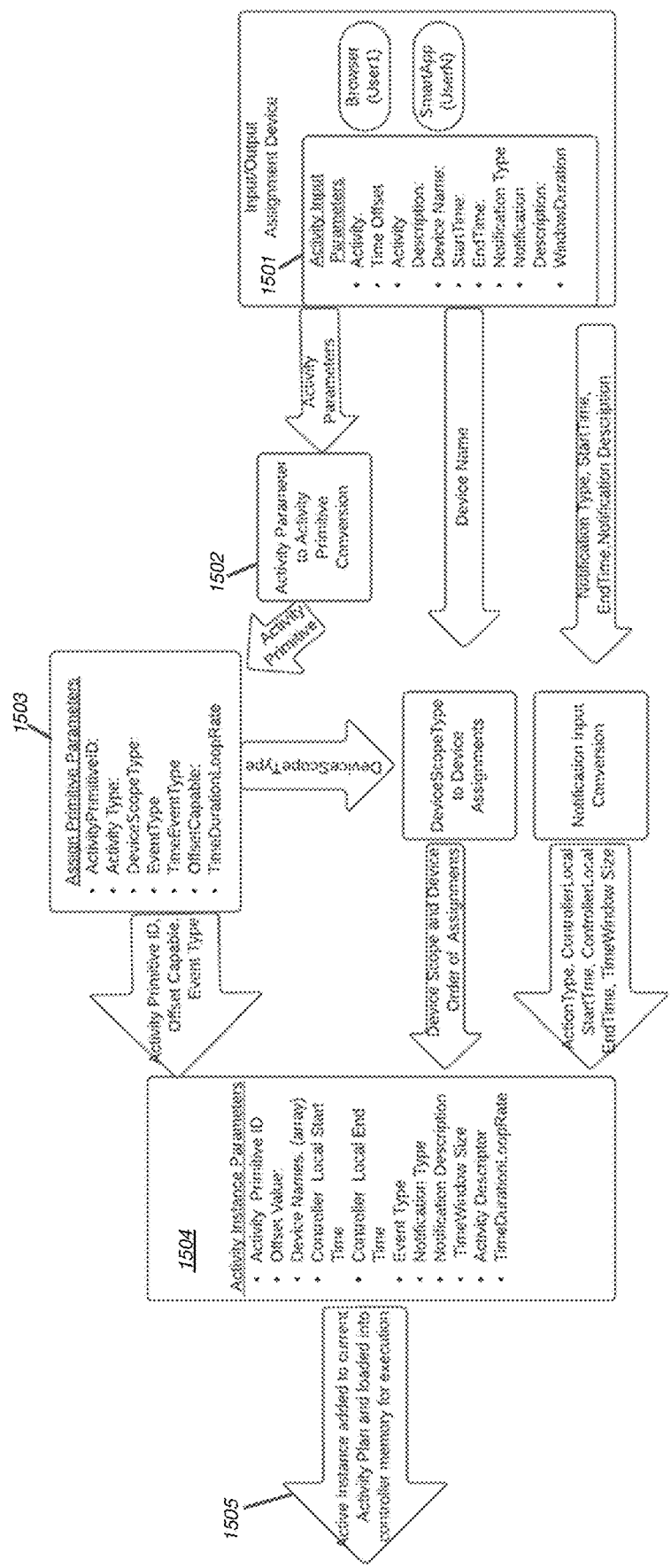
FIG. 15 is a schematic diagram illustrating a User Input Parameters to Activity Plan Assignment, according to some embodiments.

FIG. 15 is a schematic diagram illustrating a User Input Parameters to Activity Plan Assignment, according to some embodiments. In accordance with some embodiments, specification of an activity plan may be limited to one or more individuals who are given a role of "plan administrator." A designated activity plan administrator uses an activity editor (FIG. 12*a*) to input (act 1501) the following parameters:

1) Activity—this is a preselected set of activities that are assigned to one type of activity primitive. This is shown in act. An example would be a morning milestone, which expects an event to occur in a selected location by a certain time. That expected time is surrounded by a static time window with start and end times equally separated from the expected time to ensure that event did in a time frame near the expected time.
2) Offset Offset provides a way to move expected time windows by a value defined in minutes in a plus or minus direction.
3) Activity Description—A textual description of the activity plan being created. Referenced by the activity engine when the activity administrator reviews what activities are active in the current Activity Plan. The Activity Description aids the administrator in identifying the purpose of specific; activity instance.
4) Device Name—the physical sensor that represents the event of interest. In the kitchen example the physical sensor located in the kitchen would be label with a name that indicates its location in the premise, i.e. 'KITCHEN'. This is represented as the initiating sensor in the example. For activity primitives that require a completion sensor, the administrator will be prompted to identify the completion sensor.
5) StartTime—the time that the static time window will begin its search for the kitchen event.
6) Endtime—The time that the static time window would close and a determination if the specific sensor was actuated. This time is when the controller will evaluate the time window for specific sensor actuation.
7) Notification Color—administrator can set action type to Informational by selecting the color green or WarningToCritical by selecting the yellow color. For Action Notification type the value is set to blue. In the event that the sensor fails to actuate the action type is sent from the controller along with the notification count (FIG. 16 act 1601) if the action type is WarningToCritical. Informational action types do not carry a notification count.
8) Notification Description—this is the textual notification message sent to posting thread when the notification is posted.

Once all parameters are entered the activity engine creates an activity instance that will be updated into the Activity Engine's Activity Plan. The Activity Plan can support an unlimited number of active instances with the properties of the instance populated with the administrators' input data. Based on the selected activity primitives shown in act 1503, the offSetCapable property determines if a plan administrator can slide the activities window for that instance either forward or backward temporarily in time.

Act 1504 is the full instantiation of the activity plan. Each activity instance is installed in the activity engine database. When the administrator is done adding activities, a submit button is pressed which tells the activity engine to bundle all of the activities into a single activity plan. Along with the plan is the EventLoopRate which is set to either 5 or 10 minutes. This property will tell the controller how often to check for activity on the premise once the plan is active. Act 1505 is the addition of the ControllerID to route the Activity Plan to the proper controller.

Routing the Activity Plan to the may be done using known networking communications or in any other suitable way. Routing the activity plan may configure the controller to sensor outputs in accordance with the plan to generate notifications, which may be returned to the central server, in accordance with some embodiments.

Figure 16:
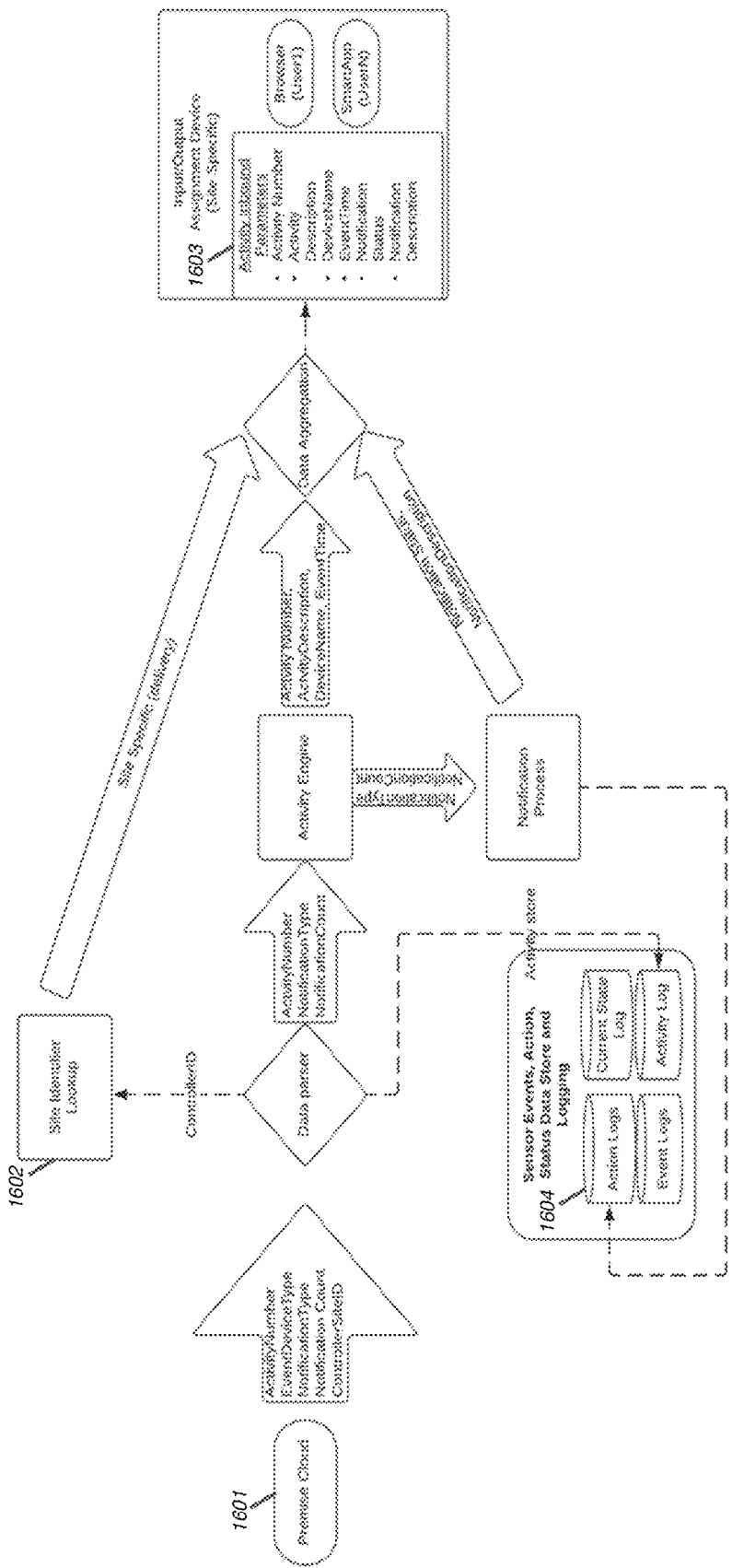
FIG. 16 is a schematic diagram illustrating an Activity Notification from Premise Cloud to Assigned Caregiver/Care Partner Site Clients, according to some embodiments.

FIG. 16 is a schematic diagram illustrating an Activity Notification from Premise Cloud to Assigned Caregiver/Care Partner Site Clients, according to some embodiments. The activity plan comprises in its action type an indication of a level of interest or concern to a specific movement or activity in a defined area or premise. The controller device is configured to selectively generate a message to the application server which will distribute the appropriate response to a user. The response embodies data as a notification from the premises indicating the specific movement or activity, the message being selectively generated based on the level of interest or concern indicated for the specific movement or activity.

At the central server, data incoming for notification is parsed to identify the premise that the Controller sending the notification is assigned. The Activity Number is used with the gathered premise information to access the activity description assigned to that activity number. The notification description uses the Activity process to access the notification description. The activity description, the notification description, notification color status, and the time of the event are returned the notification observers as inbound parameters. Following numbered items are referenced in act 1601 in FIG. 16.

1) Activity Number—Referenced in FIG. 12 act 1201 defined as the sequential number as it occurs in the controller and in the activity engines database. Number begins at 1 and has no upper range.
2) EventDeviceType—the type of physical or synthetic type of actuation. For physical sensors the types have values of 'motion', 'contact open', for temperature 'temperature', for moisture 'moisture'. For synthetic event types, used for the premiseNoActivity primitive reference in Detailed Description, subsection Activity Plan, line item 7, the value is 'synthetic'.

3) NotificatonType—one of Informational (I), WarningToCritical (WTC), Action (A). Informational is for notifying notification observers of an event. It does not carry any follow up interest in the event. The WarningToCritical has follow on interest and escalates to critical (indicated by color RED) if notification observers fail to acknowledge the WTC early notifications. ACTION type invokes control commands to identified devices (Open, Close, turn on, turn off) as a result of the activity primitive notification conditions being met.
4) NotificationCount—Defined as the number of times the exception activity (activity not is abnormal and not expected) notification has been sent to the application web services from the premise cloud. This increases for unacknowledged WTC action types but is always one for Informational.
5) ControllerID—the unique ID of the controller that is sending the notification. Used for routing to the proper notification observers.

Act 1602 references the Controller identifier is used to determine the site associated with receiving the notification. The site specific information is used to determine the posting thread that will receive the notification.

From the activity number the activity engine will access the activity, activity description, the device name and the time that the notice arrived. It will also send the action type and notification count to the notification process. From these values the notification color and notification description are aggregated with the activity, activity description, time of the event and delivered to the proper posting thread as referenced in FIG. 16. Act 1603.

Figure 17:
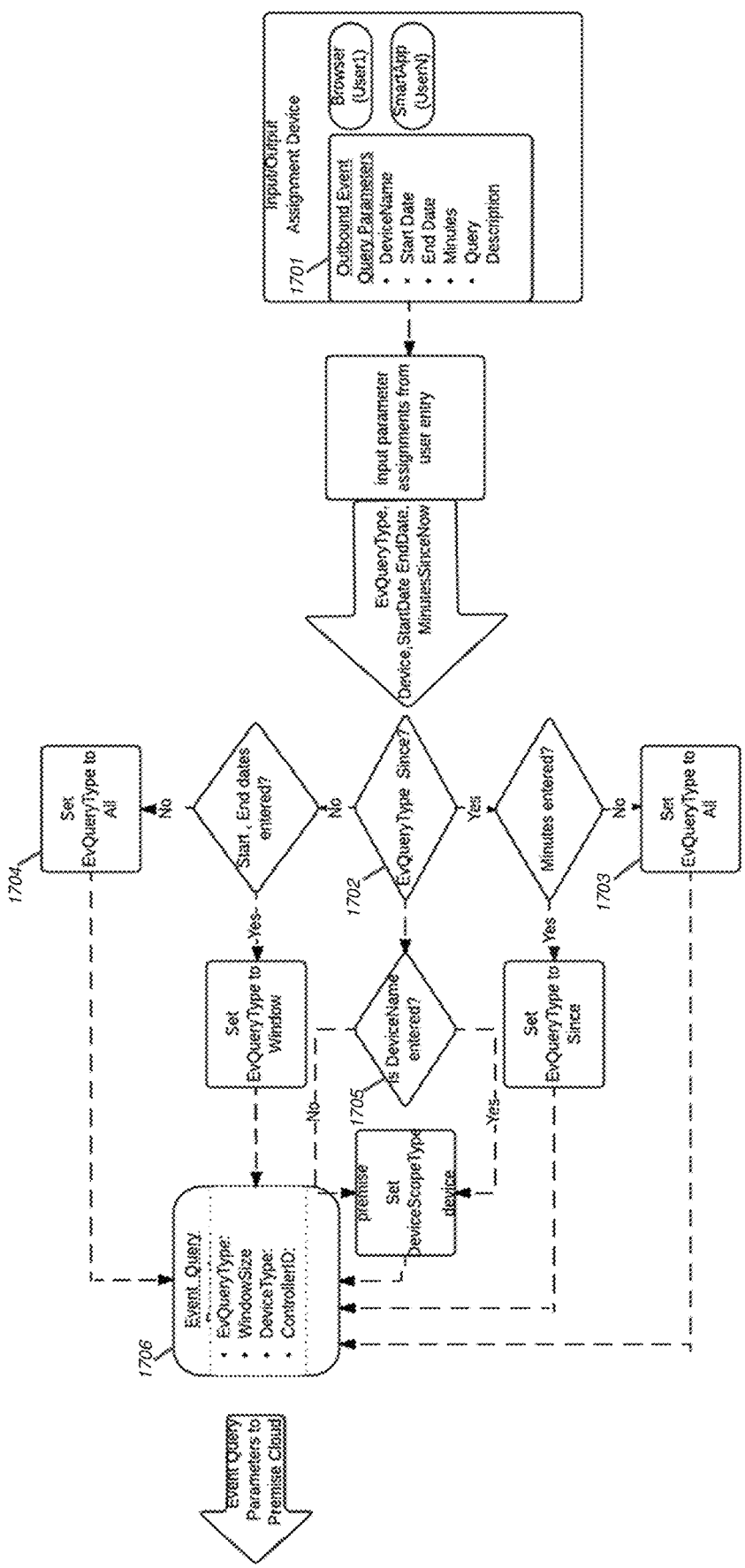
FIG. 17 is a schematic diagram illustrating an Event Query Request from Assigned Care Giver/Care Partner to Premise Cloud, according to some embodiments.

FIG. 17 is a schematic diagram illustrating an Event Query Request from Assigned Care Giver/Care Partner to Premise Cloud, according to some embodiments. Periodically, notification observers require additional information from the controllers to gather more information about current status of activity on the premise. Parameters for a request are combinations of physical sensors and time windows and the type of query (command) request. The controller can be requested to report additional status on the inhabitant. By using combinations of parameter values, the controller can be further configured to detect current or last location based on the last motion or contact sensor actuated. Data values set to the following parameters permit notification observers to customize additional (room, hallway, frontdoor, etc.) location data the duration of time in that location. FIG. 17 act 1701 references these parameters:
1) DeviceName—values of either a specific sensor, array of physical sensors, or the entire premise of sensors.
2) StartTime—For event types requiring a time window. Time to begin the search for physical sensor status.
3) EndTime—For event types requiring a time window. Time to end the search for physical sensor status.
4) Minutes—For event types requiring a time window that begins minutes from NOW and ends with the current time (most recent time or NOW).
5) Event Query type—these types determine which parameters are required for query operation. For example, query type: AllRecentMotionEvents, requires no specific sensor in the DeviceName parameter field but does require a minutes value since the type is requesting for recent (minutes past to present). A specific Query type: DeviceTimeWindow requires a specific DeviceName and specific start and end times to limit sensor status to a single sensor and a time window. Query type also define methods for searching for devices of a specific type (i.e. 'motion', contact ', open') with time window parameters associated with them.

Act 1702 shows the query type determines the parameters to be processed in the execution. If the type value is 'Since' then the minutes are determine the time back. If minutes are not entered, then the EvQueryType is set to 'All' which implies that no time window is entered meaning all events are requested (FIG. 17 act 3) from the controller with no beginning time value.

Act 1704 will also reset EvQueryType to 'All' if start and end time parameters are not entered.

Act 1705 point to the DeviceName as either a specific deviceName or to premise. If no value entered for deviceName it defaults to premise.

Act 1706 references the populated parameter entries prior to communication with the controller via the premise cloud using the controllerID for routing purposes.

Figure 18:
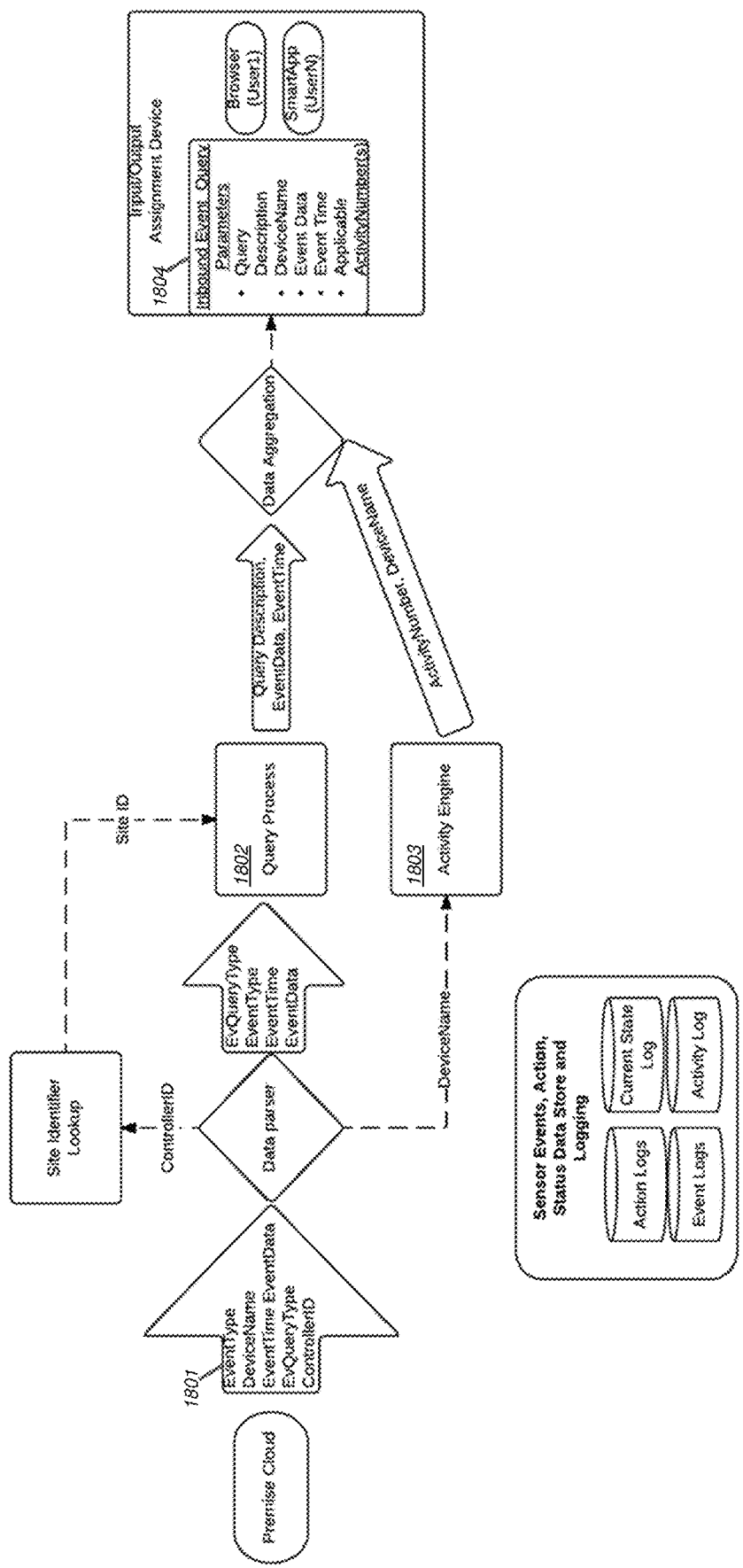
FIG. 18 is a schematic diagram illustrating an Event Query Return Process, according to some embodiments.

FIG. 18 is a schematic diagram illustrating an Event Query Return Process, according to some embodiments. Act 1801 references the populated (values assigned) parameters returned from the controller via the premise cloud. The parameters may be defined as follows:
1) EventType: one of the physical sensor types defined as either 'motion', 'contact', 'temperature', 'moisture'.
2) DeviceName: an assigned name to a physical sensor unique to that premise controller. Can also have the value of 'premise' which is interpreted by the Activity Engine (act 1803) as all devices known to the premise controller.
3.) EventTime: time that the controller recorded the sensors actuation, referred to as the event.
4) EventData: the value of event at the time of actuation. For motion type the value is either 'motion' or 'No motion'. For contact type a value of 'open' or 'close'. For temperature, a number value representing either Fahrenheit or Celsius. For moisture, a number greater than a set water density.
5) EvQueryType is the same EvQueryType value from the originating request. It serves as acknowledgement to the request.
6) ControllerID: Controller identifier of the originating request. Controller ID must match the originating request stored in the Query Engines controller-Site lookup tables.

After data parsing, the parameter values are routed to the query process (act 1802) and the Activity Engine (act 1803) where the Query description is accessed along with the eventData and EventTime values. The Activity Engine performs a lookup of the ActivityNumbers using the DeviceName and the SiteID as index values to the activity plan. The ActivityNumbers, DeviceName, Query Description, EventData, EventTime are returned to the query requester (act 1804).

Figure 19:
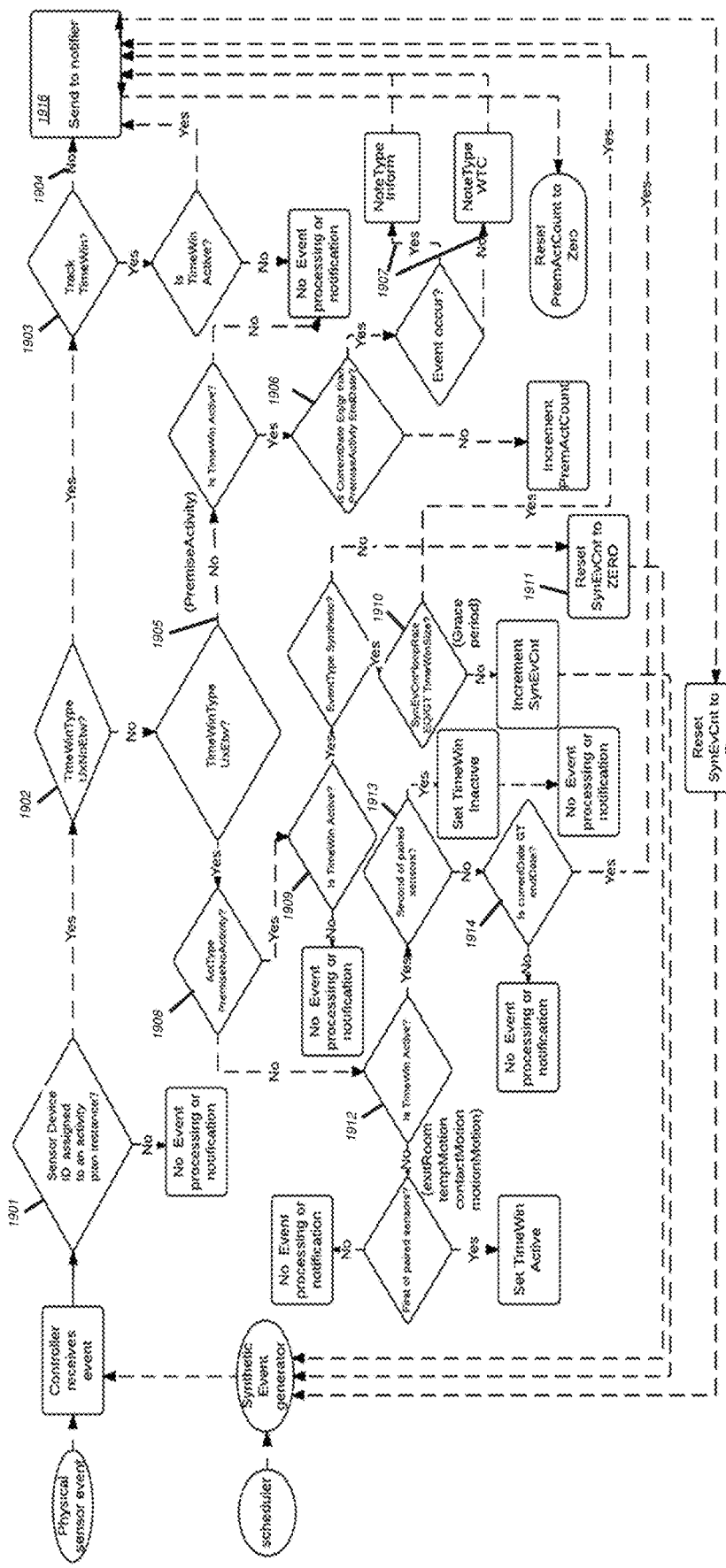
FIG. 19 is a schematic diagram illustrating a Processing Controller Events from the Activity Plan Configuration, according to some embodiments.

FIG. 19 is a schematic diagram illustrating a Processing Controller Events from the Activity Plan Configuration, according to some embodiments. The premise controller is the gatekeeper for generating notifications to the application, which may be executing on a computing device, such as server. Act 1901 begins the initial step to notification if the active (most recent actuated) sensor is part of an activity plan. Act 1902 focuses the process on the time window type attached to the event. If the TimeWinType is UxNoEtw (Unexpected No Event time window) then no dynamic window is created. Activity plans support selected time windows referenced in act 1903 and act 1208 (FIG. 12) where the activity primitive is 'premiseActvityNow' (See activity instances and FIG. 12 acts 2016 and 2018). This primitive requires immediate processing of the event and a determination if notification is required. An enabled window (FIG. 12 act 1217) can be assigned to the activity instance which limits when notification is active. The default of not setting an enabling window is notification occurs (act 1904).

If TimeWinType is not uxNoEtw then the next value examined is uxEtw (Unexpected Event time window). This type is supported by activity primitives sequencedActvity, tempMotion, contactMotion, motionMotion, premiseNoActivity. See FIG. 12 acts 1219, 1220, 1221, 1222,1223 for activity instances supporting these primitives. If TimeWinType is not uxEtw, then it defaults to exEtw which is supported by the single primitive premiseActivity show in FIG. 19 act 1905. If premiseActivity time window is active, that is, current time is between start time and end time, then the time window is tested for completion (FIG. 19 act 1906) of an expected event and the action type defined by the action type defined in the activity plan (see FIG. 12. Act 1224) is executed in the event it fails to occur (FIG. 19 act. Notifications are sent regardless of the event occurring. However whether the event did occur determines the notifications DeliveryType value (FIG. 20 act 2001) to the notification process. If the event occurred at some point in the time window, the action type is informational. If the event never occurs in the time window, a action type of WTC (WarningtoCritical) (act 1907). The notifier processing of the event data is determined by the notificationType covered in FIG. 20.

If the TimeWinType is uxEtw (act 1908) and the activity primitive is PremiseNoActivity then the time window is determined to be active (act 1909). If active then the event generated was synthetic meaning that normal expected activity was not captured by any physical sensors and to represent this no activity the activity plan tells the controller to use the OS scheduler to systematically scan the physical sensors for any activity since the first 'no activity' event occurred. After scanning for physical sensor activity in the prescribed time window (FIG. 12 act 1225) notification observers are notified if period of no activity exceeds the grace period setting (act 1910). If during the grace period if a physical sensor is actuated, the synthetic event counter is reset to zero (act 1911) and the time window that is defined as the grace period is removed.

If the activity primitive is not premiseNoActvity while the TimeWinType is uxEtw then it's one of the four primitives: sequencedActivity, tempMotion, contactMotion, motionMotion (described in the Detailed Description section, under the Activity Plan subsection, line items 2, 4, 5, 6). If the dynamic time window is active (act 1912) and the event was the result of the second sensor of the pair actuated, then the time window is removed and event processing is completed and no notification sent (act 1913). If it is not the second sensor and the time window is expired, then a notification is sent (act 1914). If the event is the initiating sensor actuation, then the time window is set to active. If the event does not belong to either the initiating (first sensor of pair) or the completion sensor (second sensor of pair) the event is ignored and no notifications sent (act 1915).

Figure 20:
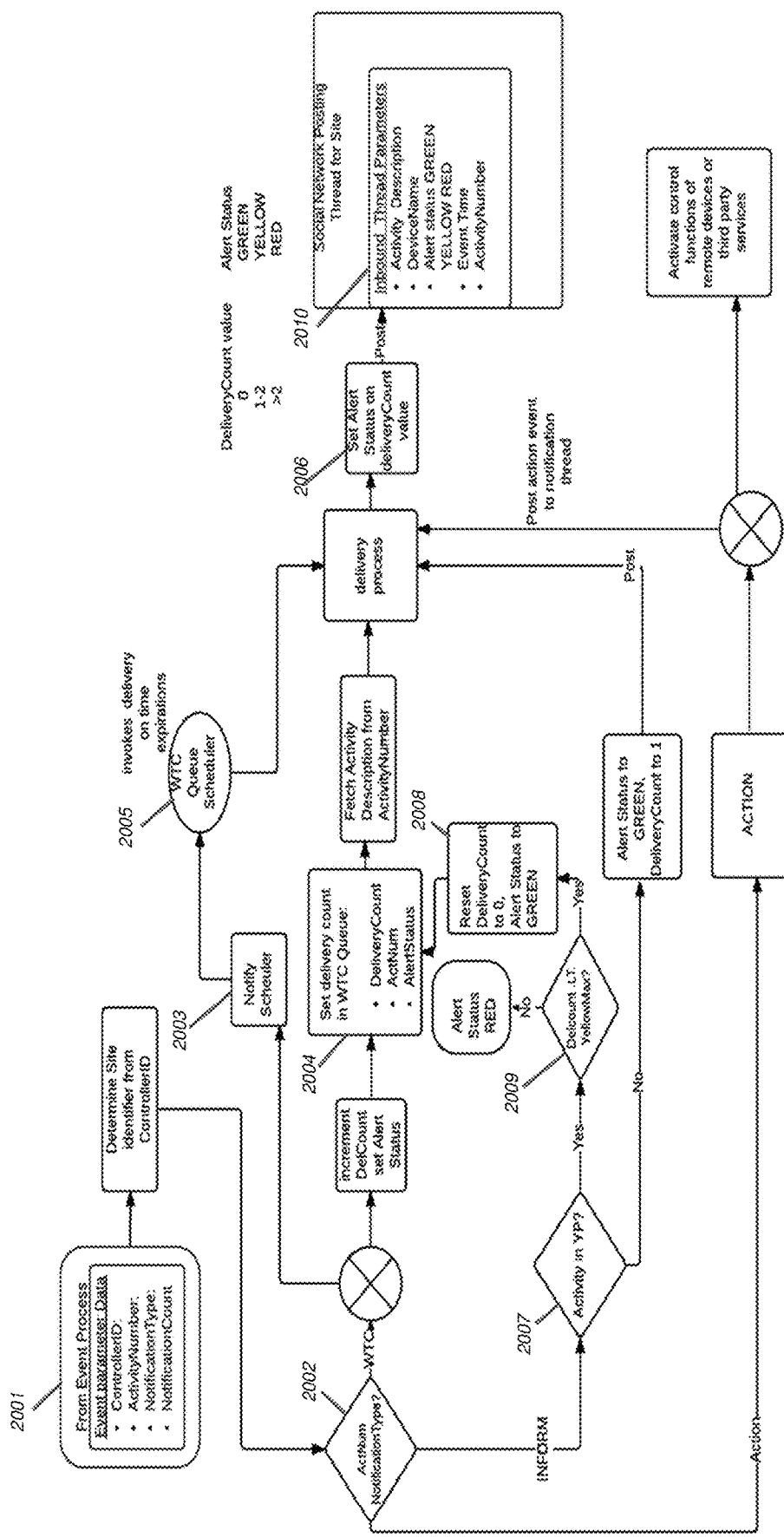
FIG. 20 is a schematic diagram illustrating a Notification Event to Posting Thread, according to some embodiments.

FIG. 20 is a schematic diagram illustrating a Notification Event to Posting Thread, according to some embodiments. FIG. 20 illustrates processing that may be performed in a server or other computing device receiving notifications from one or more controllers. The notifications may be processed by software executing on the computing device, in accordance with the processing steps described herein or other suitable processing.

Act 2001 marks the delivery of the event process with the following event parameters:
1) ControllerID—the unique identifier of the controller sending the event data.
2) ActivityNumber—the number associated to the activity instance contained in the activity plan.
3) NotificationType—one of either 'Informational' (I) or WarningToCriticar (WTC). A type of Informational delivers one notification to the notification observers and then removes the time window if one is associated. WTC delivers a notification and then observes the NotificationCount to determine the alert color and the number of notifications to send. ACTION types are sent once and non recurring.
4) NotificationCount—the total number of notifications sent for this time window.

After the site identifier has been determined, the action type determines the processing of the event. If its WTC, the scheduler is notified of the WTC (act 2005) and sets the total count in its queue for that time window instance (act 2004). The queue size indicates the number of notifications remaining for that time window instance. The notifier fetches the activity description as it was defined by the activity administrator. It then passes the activity description, activity number, the alert status based on the deliveryCount value (act 2006).

If the action type is Informational and if the time window for this activity number notification state is WTC (act 2007) the notifier checks the deliveryCount to determine if the activity window can be canceled by determining if the color status is 'YELLOW'. If it is, the time window can be canceled and the time window and exception status removed (act 2008). If color status is RED, then a manual reset is required to remove the time window and exception status. The event is ignored (act 2009).

The target destination is the posting thread (act 2010).

Figure 21:
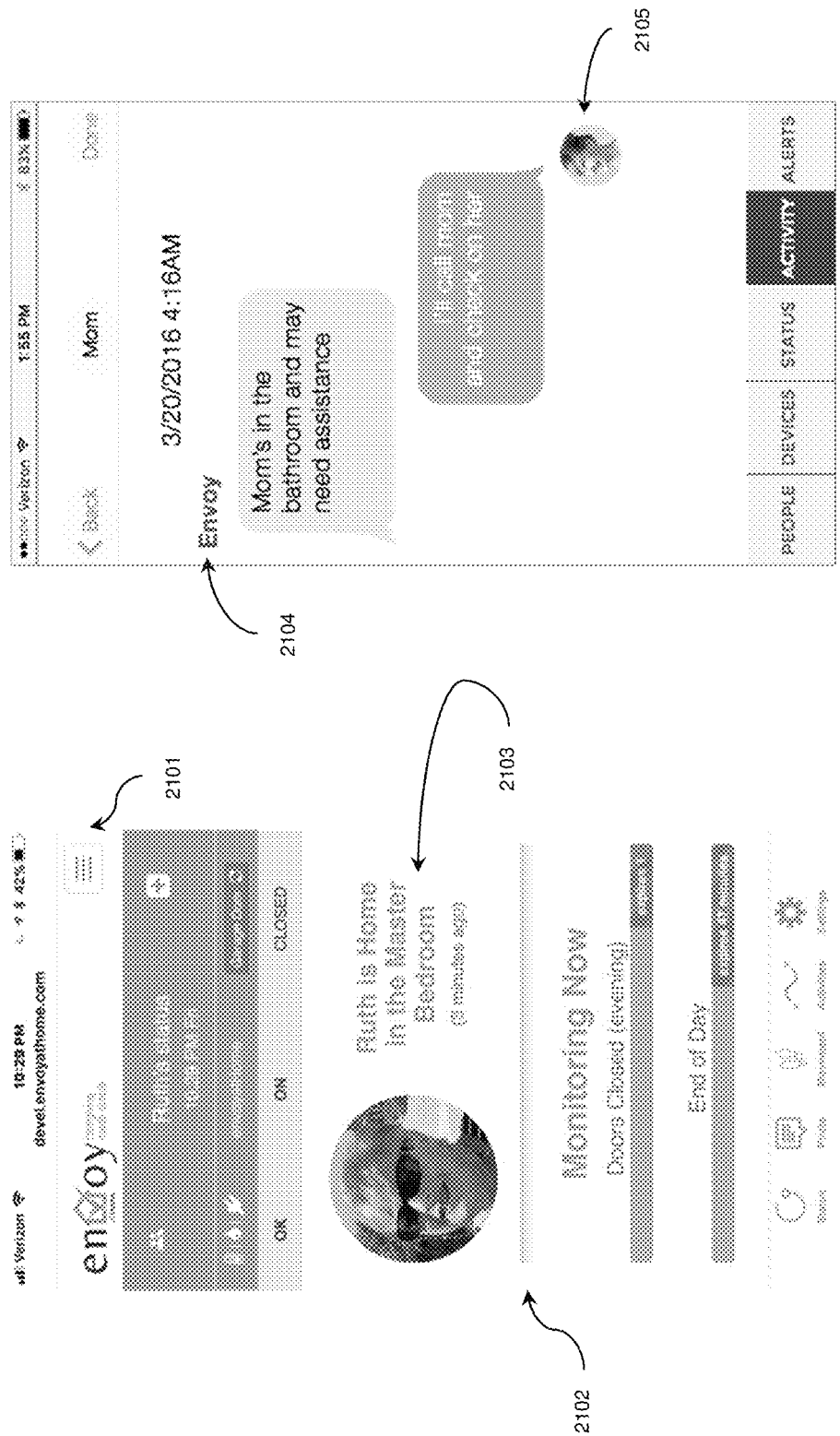
FIG. 21 is a schematic diagram illustrating a Controller Posts to the Notification Observer's Posting Thread, according to some embodiments.

FIG. 21 is a schematic diagram illustrating a Controller Posts to the Notification Observer's Posting Thread, according to some embodiments. FIG. 21 depicts two user interface screens, a sample status and an event posting thread. These user interfaces may appear on a computing device of a user or users, such as a user designated as a caregiver. In accordance with some embodiments, the computing device receiving and processing notifications may generate messages in accordance with actions specified in the activity plan. The messages, for example, may be received and processed by an app executing on a smart phone of one or more users associated with the premises from which the notification originated.

The users to receive the message may be identified based on role, such as those assigned a role of caregiver. The selected users may further depend on context, such as time of the notification. A user, for example, may be designated as a night caregiver or a day caregiver, and the user to receive the notification may depend on the time of day.

2101 shows the menu item to access additional features, settings, etc. 2102 has a dual function 1) depicts current status and 2) it can be pressed by a user to acknowledge an event (e.g. RED OR YELLOW status). 2103 shows the last known location and time. 2104 represents the controller message events. These can be informational messages or for time windows that expired to RED status or were YELLOW. 2105 is a response or reply from any of the message thread participants.

A system as described herein may be implemented with computing devices, with some computing devices configured as one or more of the following: premises controllers, user interface terminals and a server to execute an application, as described herein.

The computing devices may be special purpose computing system or configurations, which, in some embodiments, may be created by programming a general purpose computing device. Examples of well-known computing systems, environments, and/or configurations that may be suitable for use with the invention include, but are not limited to, personal computers, server computers (including those implementing cloud computing or data services), smartphones, tablets, hand-held or laptop devices, multiprocessor systems, microprocessor-based systems, set top boxes, programmable consumer electronics, network PCs, minicomputers, mainframe computers, distributed computing environments that include any of the above systems or devices, and the like. Some of the elements in a conventional computing system may not be present, depending on the specific role to be played by the computing device. Alternatively, additional elements may be present in some implementations.

The computing environment may execute computer-executable instructions, such as program modules. Generally, program modules include routines, programs, objects, components, data structures, etc. that perform particular tasks or implement particular abstract data types. Some embodiments may also be practiced in distributed computing environments where tasks are performed by remote processing devices that are linked through a communications network. These distributed systems may be what are known as enterprise computing systems or, in some embodiments, may be "cloud" computing systems. In a distributed computing environment, program modules may be located in both local and/or remote computer storage media including memory storage devices.

Figure 22:
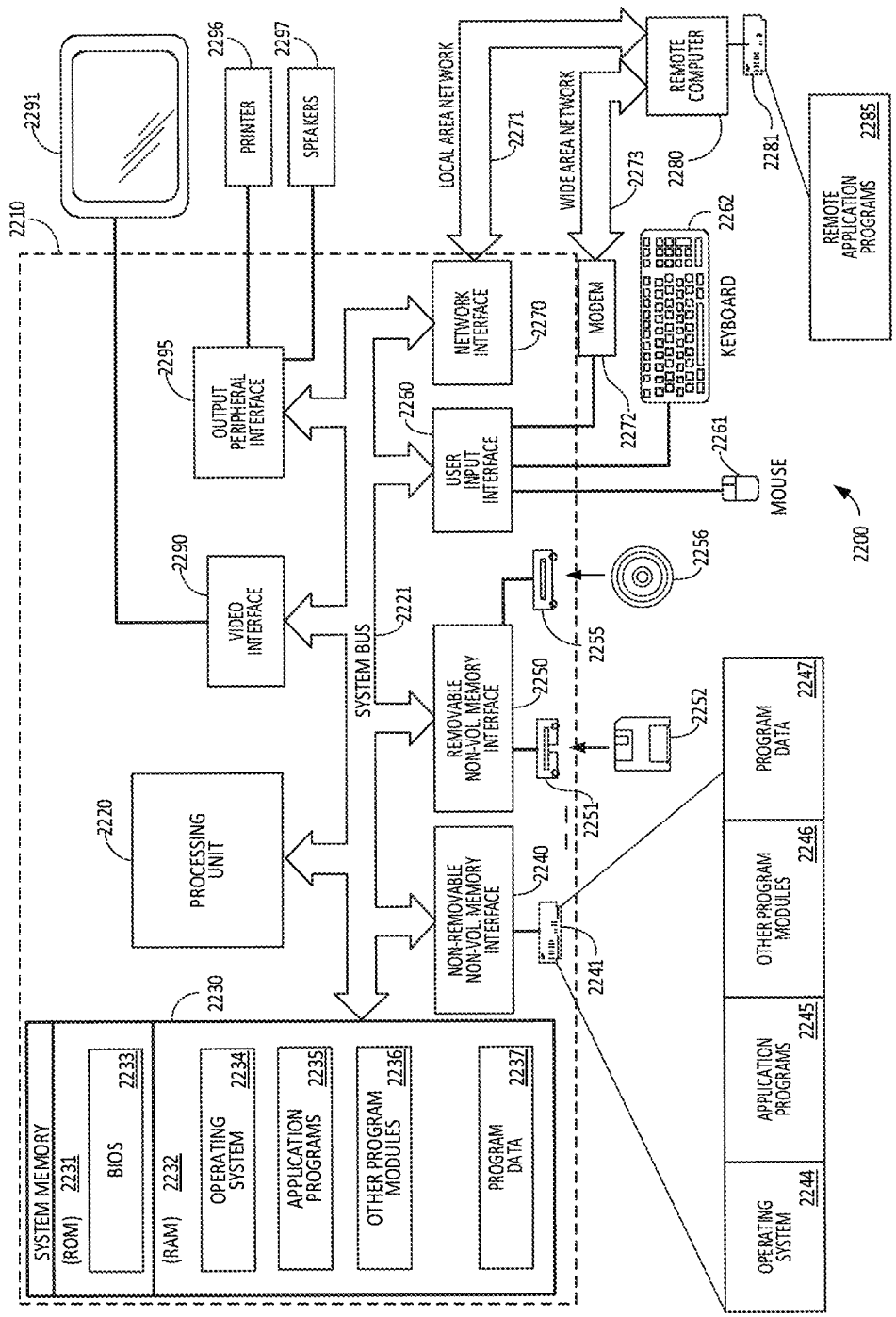
FIG. 22 is a block diagram of an exemplary computing system, according to some embodiments.

With reference to FIG. 22, an exemplary system for implementing the invention includes a general purpose computing device in the form of a computer 2210. Components of computer 2210 may include, but are not limited to, a processing unit 2220, a system memory 2230, and a system bus 2221 that couples various system components including the system memory to the processing unit 2220. The system bus 2221 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

Computer 2210 typically includes a variety of computer readable media. Computer readable media can be any available media that can be accessed by computer 2210 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 2210.

Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 2230 includes computer storage media in the form of volatile and/or nonvolatile memory such as read only memory (ROM) 2231 and random access memory (RAM) 2232. A basic input/output system 2233 (BIOS), containing the basic routines that help to transfer information between elements within computer 2210, such as during start-up, may be stored in ROM 2231. RAM 2232 may contain data and/or program modules that are immediately accessible to and/or presently being operated on by processing unit 2220. By way of example, and not limitation, FIG. 22 illustrates operating system 2234, application programs 2235, other program modules 2236, and program data 2237.

The computer 2210 may also include other removable/non-removable, volatile/nonvolatile computer storage media. By way of example only, FIG. 22 illustrates a hard disk drive 2241 that reads from or writes to non-removable, nonvolatile magnetic media. Such a hard disk drive may be implemented by a rotating disk drive or as a solid state drive, such as is implemented with FLASH memory.

FIG. 22 also illustrates a slot 2251 that reads from or writes to a removable, nonvolatile memory 2252, such as a memory stick or FLASH memory, and an optical disk drive 2255 that reads from or writes to a removable, nonvolatile optical disk 2256 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 2241 may be connected to the system bus 2221 through a non-removable memory interface such as interface 2240, and slot 2251 and optical disk drive 2255 may be connected to the system bus 2221 by a removable memory interface, such as interface 2250. However, it should be appreciated that, in some embodiments, some or all of the computer readable media available to a device may be accessed over a communication network.

The drives and their associated computer storage media discussed above and illustrated in FIG. 22, provide storage of computer readable instructions, data structures, program modules and other data for the computer 2210. In FIG. 22, for example, hard disk drive 2241 is illustrated as storing operating system 2244, application programs 2245, other program modules 2246, and program data 2247. Note that these components can either be the same as or different from operating system 2234, application programs 2235, other program modules 2236, and program data 2237. Operating system 2244, application programs 2245, other, program modules 2246, and program data 2247 are given different numbers here to illustrate that, at a minimum, they are different copies.

A computing environment may include one or more input/output devices. Some such input/out devices may provide a user interface. A user may enter commands and information into the computer 2210 through input devices such as a keyboard 2262 and pointing device 2261, depicted as a mouse. However, other forms of pointing devices may be used, including a trackball, touch pad or touch screen. Other input devices (not shown) may include a microphone, joystick, game pad, satellite dish, scanner, or the like. The microphone, for example, may support voice input, which may be recorded as an audio file or may be translated, such as using speech recognition, to a text format for further processing. These and other input devices are often connected to the processing unit 2220 through a user input interface 2260 that is coupled to the system bus, but may be connected by other interface and bus structures, such as a parallel port, game port or a universal serial has (USB).

The computing device may include one or more output devices, including an output device that may form a portion of a user interface. A monitor 2291 or other type of display device may also connected to the system bus 2221 via an interface, such as a video interface 2290, to form a visual output device. In addition to the monitor, computers may also include other peripheral output devices such as speakers 2297 and printer 2296, which may be connected through an output peripheral interface 2295. The speaker, for example, may enable output via synthesized voice or in any other suitable way.

The computer 2210 may operate in a networked environment using logical connections to one or more remote computers, such as a remote computer 2280. The remote computer 2280 may be a personal computer, a server, a router, a network PC, a peer device or other common network node, and typically includes many or all of the elements described above relative to the computer 2210, although only a memory storage device 2281 has been illustrated in FIG. 22. The logical connections depicted in FIG. 22 include a local area network (LAN) 2271 and a wide area network (WAN) 2273, but may also include other networks. Such networking environments are commonplace in offices, enterprise-wide computer networks, intranets and the Internet. Alternatively or additionally, the WAN may include a cellular network.

When used in a LAN networking environment, the computer 2210 is connected to the LAN 2271 through a network interface or adapter 2270. When used in a WAN networking environment, the computer 2210 typically includes a modem 2272 or other means for establishing communications over the WAN 2273, such as the Internet. The modem 2272, which may be internal or external, may be connected to the system bus 2221 via the user input interface 2260, or other appropriate mechanism.

In a networked environment, program modules depicted relative to the computer 2210, or portions thereof, may be stored in the remote memory storage device. By way of example, and not limitation, FIG. 22 illustrates remote application programs 2285 as residing on memory device 2281. It will be appreciated that the network connections shown are exemplary and other means of establishing a communications link between the computers may be used.

Depending on the nature of the computing device, one or more additional elements may be present. For example, a smart phone or other portable electronic device may include a camera, capable of capturing still or video images. In some embodiments, a computing device may include sensors such as a global positioning system (GPS) to sense location and inertial sensors such as a compass, an inclinometer and/o ran accelerometer. The operating system may include utilities to control these devices to capture data from them and make it available to applications executing on the computing device.

As another example, in some embodiments, a computing device may include a network interface to implement a personal area network. Such an interface may operate in accordance with any suitable technology, including a Bluetooth, Zigbee or an 802.11 ad hoc mode, for example.

Having thus described several aspects of at least one embodiment of this invention, it is to be appreciated that various alterations, modifications, and improvements will readily occur to those skilled in the art.

As an example of possible variations, it was described above that each premise contains a controller. Such a controller may be embedded in a wireless router, wireless access point or other hardware component conventionally in a home wireless network or may be a specially added component with hardware to connect to a wireless network, or may be integrated with a sensor unit. In some embodiments, there may be more than one controller at a premise. Multiple controllers may communicate with each other or with a common controller.

Such alterations, modifications, and improvements are intended to be part of this disclosure, and are intended to be within the spirit and scope of the invention. Further, though advantages of the present invention are indicated, it should be appreciated that not every embodiment of the invention will include every described advantage. Some embodiments may not implement any features described as advantageous herein. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semi-custom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format. In the embodiment illustrated, the input/output devices are illustrated as physically separate from the computing device. In some embodiments, however, the input and/or output devices may be physically integrated into the same unit as the processor or other elements of the computing device. For example, a keyboard might be implemented as a soft keyboard on a touch screen. Alternatively, the input/output devices may be entirely disconnected from the computing device, and functionally integrated through a wireless connection.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a computer-readable medium that can be considered to be a manufacture (e.g., article of manufacture) or a machine. Alternatively or additionally, the invention may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A monitoring system configured to identify movement and status of an inhabitant of a premises, the system comprising:
   a data store comprising an activity plan comprising a plurality of primitives that define a model activity pattern for the inhabitant; and
   at least one computing device coupled to the data store, the at least one computing device configured to:
      send, over a wide area network, to a controller at the premises at least a portion of the activity plan; and
      receive from the controller at the premises notifications based on sensor data captured at the premises indicating human physical motion consistent with or in conflict with the activity plan, wherein:
      the at least one computing device comprises non-transitory computer-readable medium comprising computer executable instructions that, when executed by the at least one computing device, controls the at least one computing device to present a user interface that enables a user to specify and edit the activity plan as a plurality of primitives, each primitive reflecting at least an event and a time window so as to enable each of a plurality of users with different roles within a group providing care to the inhabitant to specify at least one primitive in the activity plan, wherein the user interface, when presented, displays a representation of a primitive and comprises interface elements to receive user input specifying a value for each of a plurality of subparts of the primitive.

2. The monitoring system of claim 1, wherein:
the activity plan comprises an indication of a level of interest or concern to a specific movement or activity in a defined area or premises; and
the at least one computing device is configured to selectively generate a message to a user in response to at least one received notification from the premises indicating the specific movement or activity, the message being selectively generated based on the level of interest or concern indicated for the specific movement or activity.

3. The monitoring system of claim 1, wherein the at least one computing device comprises an activity plan editor configured to:
receive a modification of the activity plan and modify the activity plan in the data store.

4. The monitoring system of claim 1, wherein:
the at least one computing device is further configured to detect a last location of the inhabitant based on the last physical motion or contact sensor actuated.

5. A method of operating an alerting/notification system programmed with an activity plan comprising a plurality of activity primitives, each activity primitive characterizing a potential activity of an occupant of a premises, the method comprising:
receiving the activity plan via a user interface configured to receive input from users having one of at least two roles in caring for the occupant, wherein the activity plan comprises a plurality of activity primitives, each activity primitive of the plurality of activity primitives comprising:
an activity type;
an activity time and/or timeframe; and
a notification parameter;
receiving data from a plurality of sensors;
processing the received data to identify occurrence of an event associated with at least one activity primitive of the plurality of activity primitives; and
selectively sending, based on at least the notification parameter of the at least one activity primitive, at least one message to one or more notification observers of the alerting/notification system, in accordance with the notification parameter of the at least one activity primitive and the received sensor data.

6. The method of claim 5, wherein:
the at least one activity primitive comprises a 'no activity' primitive; and
selectively sending comprises sending a message when no activity is detected for a period of time specified in connection with the at least one activity primitive.

7. The method of claim 5, wherein:
the at least one activity primitive comprises a time window and classifies movement and/or activity of the inhabitant as expected, unexpected but normal, and abnormal patterns of behavior based on occurrence and/or absence of outputs from the plurality of sensors in the time window.

8. The method of claim 7, wherein:
receiving data comprises receiving data from a plurality of sensors specified in conjunction with the at least one activity primitive.

9. The method of claim 5, further comprising:
analyzing the received data to identify trends in daily movement patterns over comparative time periods of historical activity.

10. The method of claim 5, wherein:
the one or more notification observers comprises a plurality of notification observers, at least one of which is a primary caregiver and at least one of which is an outside service; and
a computing device sends the notification in response to receiving sensor data without human intervention.

11. The method of claim 5, further comprising:
adapting at least one criterion for selectively sending at least one message to one or more notification observers based on detecting an unexpected activity pattern.

12. The method of claim 5, wherein:
the notification parameters of the at least one activity primitive comprise a notification level; and
selectively sending at least one message to one or more notification observers comprises sending a message, configured based on at least the notification level, to one of an alarm company, emergency medical provider, fire rescue, police and entities providing caregiver or care monitoring services.

13. The method of claim 5, wherein the user interface is further configured to receive, in connection with activity primitives of the activity plan, an indication of a level of interest or concern for the users.

14. At least one non-transitory computer-readable medium comprising computer executable instructions that, when executed by at least one processor in a controller coupled to a plurality of sensors at a premises, performs a method of monitoring activity of a human within the premises, the method comprising:
receiving over a network a plurality of activity primitives, each activity primitive comprising:
a time window; and
an indication of an activity detectable based on outputs of the plurality of sensors;
based on the outputs of the plurality of sensors and the plurality of activity primitives, detecting occurrence or non-occurrence of activities associated with the plurality of activity primitives and tracking a warning state associated with at least one activity primitive of the plurality of activity primitives based on the detected occurrence or non-occurrence;
communicating over the network notifications based on the warning state so as to provide a first notification and subsequent notifications that progressively escalate in urgency, based on at least the time elapsed from providing of the first notification without receiving a response from any of a plurality of individuals in a care team, such notifications associated with the at least one activity primitive; and
resetting the warning state based on receiving over the network, from any of a plurality of individuals in a care team, an indication to reset the warning state.

15. The at least one non-transitory computer-readable medium of claim 14, wherein the method further comprises:

receiving over the network a command to add an activity primitive to, and/or remove an activity primitive from, an activity plan comprising the plurality of activity primitives.

16. The at least one non-transitory computer-readable medium of claim 14, wherein:
the subsequent notifications progressively escalate based on at least a comparison of a time proportional to the size of the time window with the time elapsed from providing of the first notification without receiving a response.

17. The at least one non-transitory computer-readable medium of claim 14, wherein receiving over the network the plurality of activity primitives comprises receiving user input via a user interface of a networked server.

18. The at least one non-transitory computer-readable medium of claim 15, wherein:
the plurality of sensors comprises a first sensor and a second sensor; and
an activity primitive of the plurality of activity primitives indicates an activity based on the first sensor indicating an occupant of the premises moving past the first sensor and the second sensor indicating the occupant of the premises moving past the second sensor within a time window specified by the activity primitive.

19. The at least one non-transitory computer-readable medium of claim 15, wherein:
an activity primitive of the plurality of action primitives comprises processing to check for sensor events during the time window of the activity primitive and/or at the end of the time window of the activity primitive.

20. The at least one non-transitory computer-readable medium of claim 15, wherein:
an activity primitive of the plurality of activity primitives indicates real-time transmission of a notification in response to a sensor output that indicates an event during the time window of the activity primitive.

21. The at least one non-transitory computer-readable medium of claim 15, wherein:
an activity primitive of the plurality of activity primitives indicates processing to check for absence of sensor events during a specified time window plus a grace period following the end of the specified time window.

22. The at least one non-transitory computer-readable medium of claim 15, wherein:
an activity primitive of the plurality of activity primitives indicates processing to check for an event indicated by a second sensor within the time window of the activity primitive, the event indicated by the second sensor being associated with an event indicated by a first sensor.

23. The at least one non-transitory computer-readable medium of claim 15, wherein:
an activity primitive of the plurality of activity primitives indicates transmitting a notification when a first sensor indicates a first event and a second sensor does not indicate a second event within the time window associated with the activity primitive following the first event.

* * * * *